(12) United States Patent
Lavergne et al.

(10) Patent No.: US 7,012,079 B1
(45) Date of Patent: Mar. 14, 2006

(54) OPTICALLY PURE CAMPTOTHECIN ANALOGUES

(75) Inventors: Olivier Lavergne, Palaiseau (FR); Dennis Bigg, Gif-sur-Yvette (FR); Christophe Lanco, Dourdan (FR); Alain Rolland, Palaiseau (FR)

(73) Assignee: Societe de Conseils de Recherches et d'Applications Scientifiques (S.C.R.A.S.), (FR)

( * ) Notice: Subject to any disclaimer, the term of this patent is extended or adjusted under 35 U.S.C. 154(b) by 0 days.

(21) Appl. No.: 09/806,952

(22) PCT Filed: Feb. 24, 2000

(86) PCT No.: PCT/FR00/00461

§ 371 (c)(1),
(2), (4) Date: Apr. 5, 2001

(87) PCT Pub. No.: WO00/50427

PCT Pub. Date: Aug. 31, 2000

(30) Foreign Application Priority Data

Feb. 26, 1999 (FR) ................................. 99 02398

(51) Int. Cl.
*C07D 491/14* (2006.01)
*C07D 491/22* (2006.01)
*A61K 31/44* (2006.01)

(52) U.S. Cl. ................... 514/279; 514/283; 546/14; 546/41; 546/48

(58) Field of Classification Search .............. 546/14; 514/283
See application file for complete search history.

(56) References Cited

U.S. PATENT DOCUMENTS 5,981,542 A * 11/1999 Bigg et al. .................. 514/283
6,207,832 B1 * 3/2001 Curran et al. ................ 546/14

FOREIGN PATENT DOCUMENTS

| FR | 2757514 | | 6/1998 |
| FR | 2757515 | | 6/1998 |
| WO | 97/00876 | * | 1/1997 |
| WO | 9700876 | | 1/1997 |
| WO | 98/07727 | * | 2/1998 |
| WO | 9828304 | | 7/1998 |
| WO | 9828305 | | 7/1998 |
| WO | 9835940 | | 8/1998 |
| WO | 9911646 | | 3/1999 |

OTHER PUBLICATIONS

Laurence Lesuer-Ginot et al Cancer research vol. 59, pp. 2939-2943 1999.*
Christain Bailly et al , Biochemistry 1999, vol. 38 pp. 15556-15563. Homocamptothecin , an E-ring . . . .*
Lavergne et al, "An E-Ring . . . Activities", Bioorg. Med. Chem. Letters, vol. 7, no 17, 1997, pp. 2235-2238.
Ejima et al, "Antitumor . . . Analogues", Chemical and Pharm-aceutical Bulletin, vol. 40, no 3, Mar. 1, 1992, pp. 683-688.

* cited by examiner

*Primary Examiner*—Rita Desai
(74) *Attorney, Agent, or Firm*—Charles A. Muserlian

(57) ABSTRACT

The invention relates in particular to the compounds of general formula

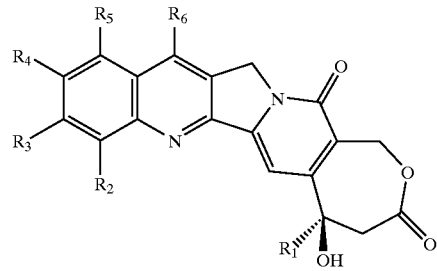

in which $R_1$, $R_2$, $R_3$, $R_4$, $R_5$, $R_6$ represent various radicals; their use as medicaments and pharmaceutical compositions containing them. These compounds are particularly useful for the treatment of cancer.

3 Claims, No Drawings

OPTICALLY PURE CAMPTOTHECIN ANALOGUES

This application is a 371 of PCT/FR00/00461 filed Feb. 24, 2000.

Camptothecin is a natural compound which has been isolated for the first time from the leaves and the bark of the Chinese plant called *camptotheca acuminata* (see Wall et al. J. Amer. Chem. Soc. 88:3888 (1966)). Camptothecin is a pentacyclic compound constituted by an indolizino[1,2-b] quinoline fragment fused with an α-hydroxylactone with six links. The carbon in position 20 which carries the α-hydroxy group is asymmetrical and confers a rotatory power on the molecule. The natural form of camptothecin has an absolute "S" configuration as regards the carbon 20 and corresponds to the following formula:

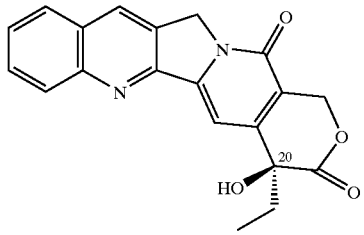

Camptothecin has an anti-proliferative activity in several cancerous cell lines, including the cell lines of human tumors of the colon, lung and breast (Suffness, M et al: The Alkaloids Chemistry and Pharmacology, Bross A., ed., Vol. 25, p. 73 (Academic Press, 1985)). It is suggested that the anti-proliferative activity of camptothecin is related to its inhibitory activity on DNA topoisomerase I.

It has been indicated that α-hydroxylactone was an absolute requirement both for the in vivo and in vitro activity of camptothecin (Camptothecins: New Anticancer Agents, Putmesil, M et al, ed., p. 27 (CRC Press, 1995); Wall M. et al, Cancer Res. 55:753 (1995); Hertzberg et al, J. Med. Chem. 32:715 (1982) and Crow et al, J. Med. Chem. 35:4160 (1992)). More recently, the applicant has perfected a new class of analogues of camptothecin, in which a β-hydroxylactone replaces the natural β-hydroxylactone of camptothecin (cf. Patent Applications WO 97/00876, WO 98/28304 and WO 98/28305).

A subject of the present Application is new β-hydroxylactonic analogues of camptothecin, the biological activity of which, expressed for example in terms of inhibitory concentrations on the proliferation of tumoral cell colonies, is, unexpectedly, superior to the activity of compounds which are already known. A subject of the invention is also the compounds previously mentioned as medicaments, pharmaceutical compositions containing them as well as a preparation process.

The invention firstly relates to the compounds of general formula (I) characterized in that they correspond either to formula $I_A$

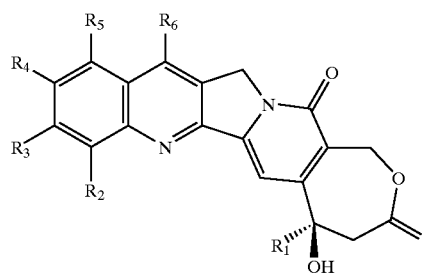

in which
R₁ represents a lower alkyl radical;
R₂, R₃, R₄ and R₅ represent, independently, H, halo or —OSO₂R₁₀;
R₆ represents H, a linear or branched alkyl radical containing 1 to 12 carbon atoms optionnally substituted by one or more halo radicals indentical or different, lower hydroxy alkyl, lower alkoxy lower alkyl, a cycloalkyl, lower cycloalkyl alkyl, nitro, halo, —(CH₂)ₘSiR₇R₈R₉ radical, or an aryl substituted or non substituted or lower aryl alkyl radical substituted or non substituted on the aryl group, the substituents of the aryl groups being identical or different and selected from: lower alkyl, hydroxy, halo, amino, lower alkyl amino, di(lower alkyl)amino, CF₃ or OCF₃;
R₇, R₈ and R₉ represent, independently, a lower alkyl radical;
R₁₀ represents a lower alkyl radical optionnally substituted by one or more halo radicals identical or different, or an aryl optionnally susbtituted by one or more lower alkyl radicals identical or different;
m is an integer comprised between 0 and 6;

it being understood that when R₂ represents H
  R₆ represents a linear or branched alkyl radical containing 7 à 12 carbon atoms, —(CH₂)ₘSiR₇R₈R₉, or an aryle group substituted by one or more substituents indentical or different and selected from di(lower alkyl)amino and OCF₃, and/or
  at least one of the radicals R₃, R₄ and R₅ represents —OSO₂R₁₀;

or one of the following formulae:
(5R)-5-ethyl-11-fluoro-5-hydroxy-4,5,13,15-tetrahydro-1H, 3H-oxepino[3',4':6,7]indolizino[1,2-b]quinoleine-3,15-dione;
(5R)-5-ethyl-9-fluoro-5-hydroxy-4,5,13,15-tetrahydro-1H, 3H-oxepino[3',4':6,7]indolizino[1,2-b]quinoleine-3,15-dione;
(5R)-12-benzyl-5-ethyl-5-hydroxy-4,5,13,15-tetrahydro-1H,3H-oxepino[3',4':6,7]indolizino[1,2-b]quinoleine-3, 15-dione;
(5R)-12-butyl-5-ethyl-5-hydroxy-4,5,13,15-tetrahydro-1H, 3H-oxepino[3',4':6,7]indolizino[1,2-b]quinoleine-3,15-dione;
(5R)-5,12-diethyl-5-hydroxy-4,5,13,15-tetrahydro-1H,3H-oxepino[3',4':6,7]indolizino[1,2-b]quinoleine-3,15-dione;
(5R)-5-ethyl-5-hydroxy-12-phenyl-4,5,13,15-tetrahydro-1H,3H-oxepino[3',4':6,7]indolizino[1,2-b]quinoleine-3, 15-dione;
(5R)-12-cyclohexyl-5-ethyl-5-hydroxy-4,5,13,15-tetrahydro-1H,3H-oxepino[3',4':6,7]indolizino[1,2-b] quinoleine-3,15-dione;

(5R)-5-ethyl-5-hydroxy-12-(4-methylphenyl)-4,5,13,15-tetrahydro-1H,3H-oxepino [3',4':6,7]indolizino[1,2-b]quinoleine-3,15-dione;

(5R)-10-chloro-5-ethyl-12-(2-fluorophenyl)-5-hydroxy-4,5,13,15-tetrahydro-1H,3H-oxepino[3',4':6,7]indolizino[1,2-b]quinoleine-3,15-dione;

(5R)-5-ethyl-9,10-difluoro-5-hydroxy-12-phenyl-4,5,13,15-tetrahydro-1H,3H-oxepino [3',4':6,7]indolizino[1,2-b]quinoleine-3,15-dione;

(5R)-5-ethyl-9-fluoro-5-hydroxy-12-phenyl-4,5,13,15-tetrahydro-1H,3H-oxepino [3',4':6,7]indolizino[1,2-b]quinoleine-3,15-dione;

(5R)-12-butyl-5-ethyl-9,10-difluoro-5-hydroxy-4,5,13,15-tetrahydro-1H,3H-oxepino [3',4':6,7]indolizino[1,2-b]quinoleine-3,15-dione;

(5R)-12-benzyl-5-ethyl-9,10-difluoro-5-hydroxy-4,5,13,15-tetrahydro-1H,3H-oxepino [3',4':6,7]indolizino[1,2-b]quinoleine-3,15-dione;

(5R)-5-ethyl-9,10-difluoro-5-hydroxy-12-propyl-4,5,13,15-tetrahydro-1H,3H-oxepino [3',4':6,7]indolizino[1,2-b]quinoleine-3,15-dione;

(5R)-5,12-diethyl-9,10-difluoro-5-hydroxy-4,5,13,15-tetrahydro-1H,3H-oxepino [3',4':6,7]indolizino[1,2-b]quinoleine-3,15-dione;

(5R)-5-ethyl-9,11-difluoro-5-hydroxy-4,5,13,15-tetrahydro-1H,3H-oxepino[3',4':6,7]indolizino[1,2-b]quinoleine-3,15-dione;

(5R)-12-butyl-5-ethyl-9,11-difluoro-5-hydroxy-4,5,13,15-tetrahydro-1H,3H-oxepino [3',4':6,7]indolizino[1,2-b]quinoleine-3,15-dione;

(5R)-5,12-diethyl-9,11-difluoro-5-hydroxy-4,5,13,15-tetrahydro-1H,3H-oxepino [3',4':6,7]indolizino[1,2-b]quinoleine-3,15-dione;

(5R)-5-ethyl-5-hydroxy-12-propyl-4,5,13,15-tetrahydro-1H,3H-oxepino[3',4':6,7]indolizino[1,2-b]quinoleine-3,15-dione;

(5R)-12-butyl-5-ethyl-9-fluoro-5-hydroxy-4,5,13,15-tetrahydro-1H,3H-oxepino [3',4':6,7]indolizino[1,2-b]quinoleine-3,15-dione (5R)-5,12-diethyl-9-fluoro-5-hydroxy-4,5,13,15-tetrahydro-1H,3H-oxepino[3',4':6,7]indolizino[1,2-b]quinoleine-3,15-dione;

(5R)-5-ethyl-5-hydroxy-12-isopentyl-4,5,13,15-tetrahydro-1H,3H-oxepino[3',4':6,7]indolizino[1,2-b]quinoleine-3,15-dione;

(5R)-5-ethyl-12-(4-fluorophenyl)-5-hydroxy-4,5,13,15-tetrahydro-1H,3H-oxepino [3',4':6,7]indolizino[1,2-b]quinoleine-3,15-dione;

(5R)-12-(2,6-difluorophenyl)-5-ethyl-5-hydroxy-4,5,13,15-tetrahydro-1H,3H-oxepino [3',4':6,7]indolizino[1,2-b]quinoleine-3,15-dione;

(5R)-12-(3,5-difluorophenyl)-5-ethyl-5-hydroxy-4,5,13,15-tetrahydro-1H,3H-oxepino [3',4':6,7]indolizino[1,2-b]quinoleine-3,15-dione;

(5R)-5-ethyl-5-hydroxy-12-(3,4,5-trifluorophenyl)-4,5,13,15-tetrahydro-1H,3H-oxepino [3',4':6,7]indolizino[1,2-b]quinoleine-3,15-dione;

(5R)-5-ethyl-5-hydroxy-12-(2,4,6-trifluorophenyl)-4,5,13,15-tetrahydro-1H,3H-oxepino [3',4':6,7]indolizino[1,2-b]quinoleine-3,15-dione;

(5R)-5-ethyl-5-hydroxy-12-(2,3,5,6-tetrafluorophenyl)-4,5,13,15-tetrahydro-1H,3H-oxepino [3',4':6,7]indolizino[1,2-b]quinoleine-3,15-dione;

(5R)-5-ethyl-5-hydroxy-12-(2,3,4,5,6-pentafluorophenyl)-4,5,13,15-tetrahydro-1H,3H-oxepino [3',4':6,7]indolizino[1,2-b]quinoleine-3,15-dione;

(5R)-5-ethyl-9-fluoro-12-(4-fluorophenyl)-5-hydroxy-4,5,13,15-tetrahydro-1H,3H-oxepino [3',4':6,7]indolizino[1,2-b]quinoleine-3,15-dione;

(5R)-12-(2,6-difluorophenyl)-5-ethyl-9-fluoro-5-hydroxy-4,5,13,15-tetrahydro-1H,3H-oxepino [3',4':6,7]indolizino[1,2-b]quinoleine-3,15-dione;

(5R)-12-(3,5-difluorophenyl)-5-ethyl-9-fluoro-5-hydroxy-4,5,13,15-tetrahydro-1H,3H-oxepino [3',4':6,7]indolizino[1,2-b]quinoleine-3,15-dione;

(5R)-5-ethyl-9-fluoro-5-hydroxy-12-(3,4,5-trifluorophenyl)-4,5,13,15-tetrahydro-1H,3H-oxepino[3',4':6,7]indolizino[1,2-b]quinoleine-3,15-dione;

(5R)-5-ethyl-9-fluoro-5-hydroxy-12-(2,4,6-trifluorophenyl)-4,5,13,15-tetrahydro-1H,3H-oxepino[3',4':6,7]indolizino[1,2-b]quinoleine-3,15-dione;

(5R)-5-ethyl-9-fluoro-5-hydroxy-12-(2,3,5,6-tetrafluorophenyl)-4,5,13,15-tetrahydro-1H,3H-oxepino[3',4':6,7]indolizino[1,2-b]quinoleine-3,15-dione;

(5R)-5-ethyl-9-fluoro-5-hydroxy-12-(2,3,4,5,6-pentafluorophenyl)-4,5,13,15-tetrahydro-1H,3H-oxepino[3',4':6,7]indolizino[1,2-b]quinoleine-3,15-dione;

(5R)-5-ethyl-9,10-difluoro-12-(4-fluorophenyl)-5-hydroxy-4,5,13,15-tetrahydro-1H,3H-oxepino[3',4':6,7]indolizino[1,2-b]quinoleine-3,15-dione;

(5R)-12-(2,6-difluorophenyl)-5-ethyl-9,10-difluoro-5-hydroxy-4,5,13,15-tetrahydro-1H,3H-oxepino[3',4':6,7]indolizino[1,2-b]quinoleine-3,15-dione;

(5R)-12-(3,5-difluorophenyl)-5-ethyl-9,10-difluoro-5-hydroxy-4,5,13,15-tetrahydro-1H,3H-oxepino[3',4':6,7]indolizino[1,2-b]quinoleine-3,15-dione;

(5R)-5-ethyl-9,10-difluoro-5-hydroxy-12-(3,4,5-trifluorophenyl)-4,5,13,15-tetrahydro-1H,3H-oxepino[3',4':6,7]indolizino[1,2-b]quinoleine-3,15-dione;

(5R)-5-ethyl-9,10-difluoro-5-hydroxy-12-(2,4,6-trifluorophenyl)-4,5,13,15-tetrahydro-1H,3H-oxepino[3',4':6,7]indolizino[1,2-b]quinoleine-3,15-dione;

(5R)-5-ethyl-9,10-difluoro-5-hydroxy-12-(2,3,5,6-tetrafluorophenyl)-4,5,13,15-tetrahydro-1H,3H-oxepino[3',4':6,7]indolizino[1,2-b]quinoleine-3,15-dione;

(5R)-5-ethyl-9,10-difluoro-5-hydroxy-12-(2,3,4,5,6-pentafluorophenyl)-4,5,13,15-tetrahydro-1H,3H-oxepino[3',4':6,7]indolizino[1,2-b]quinoleine-3,15-dione;

(5R)-5-ethyl-9,11-difluoro-12-(4-fluorophenyl)-5-hydroxy-4,5,13,15-tetrahydro-1H,3H-oxepino[3',4':6,7]indolizino[1,2-b]quinoleine-3,15-dione;

(5R)-12-(2,6-difluorophenyl)-5-ethyl-9,11-difluoro-5-hydroxy-4,5,13,15-tetrahydro-1H,3H-oxepino[3',4':6,7]indolizino[1,2-b]quinoleine-3,15-dione;

(5R)-12-(3,5-difluorophenyl)-5-ethyl-9,11-difluoro-5-hydroxy-4,5,13,15-tetrahydro-1H,3H-oxepino[3',4':6,7]indolizino[1,2-b]quinoleine-3,15-dione;

(5R)-5-ethyl-9,11-difluoro-5-hydroxy-12-(3,4,5-trifluorophenyl)-4,5,13,15-tetrahydro-1H,3H-oxepino[3',4':6,7]indolizino[1,2-b]quinoleine-3,15-dione;

(5R)-5-ethyl-9,11-difluoro-5-hydroxy-12-(2,4,6-trifluorophenyl)-4,5,13,15-tetrahydro-1H,3H-oxepino[3',4':6,7]indolizino[1,2-b]quinoleine-3,15-dione;

(5R)-5-ethyl-9,11-difluoro-5-hydroxy-12-(2,3,5,6-tetrafluorophenyl)-4,5, 13,15-tetrahydro-1H,3H-oxepino[3',4':6,7]indolizino[1,2-b]quinoleine-3,15-dione;

(5R)-5-ethyl-9,11-difluoro-5-hydroxy-12-(2,3,4,5,6-pentafluorophenyl)-4,5, 13,15-tetrahydro-1H,3H-oxepino[3',4':6,7]indolizino[1,2-b]quinoleine-3,15-dione;

(5R)-5-ethyl-9-fluoro-5-hydroxy-12-propyl-4,5,13,15-tetrahydro-1H,3H-oxepino[3',4':6,7]indolizino[1,2-b]quinoleine-3,15-dione;

(5R)-5-ethyl-9-fluoro-5-hydroxy-12-(3,3,3-trifluoropropyl)-4,5,13,15-tetrahydro-1H,3H-oxepino[3',4':6,7]indolizino[1,2-b]quinoleine-3,15-dione;

(5R)-5-ethyl-9-fluoro-5-hydroxy-12-isopentyl-4,5,13,15-tetrahydro-1H,3H-oxepino [3',4':6,7]indolizino[1,2-b]quinoleine-3,15-dione;

(5R)-5-ethyl-9-fluoro-5-hydroxy-12-pentyl-4,5,13,15-tetrahydro-1H,3H-oxepino [3',4':6,7]indolizino[1,2-b]quinoleine-3,15-dione;

(5R)-5-ethyl-9-fluoro-5-hydroxy-12-phenethyl-4,5,13,15-tetrahydro-1H,3H-oxepino [3',4':6,7]indolizino[1,2-b]quinoleine-3,15-dione;

(5R)-12-(2-cyclohexylethyl)-5-ethyl-9-fluoro-5-hydroxy-4,5,13,15-tetrahydro-1H,3H-oxepino [3',4':6,7]indolizino[1,2-b]quinoleine-3,15-dione;

(5R)-12-(3,3-dimethylbutyl)-5-ethyl-9-fluoro-5-hydroxy-4,5,13,15-tetrahydro-1H,3H-oxepino [3',4':6,7]indolizino[1,2-b]quinoleine-3,15-dione;

(5R)-5-ethyl-9,10-difluoro-5-hydroxy-12-propyl-4,5,13,15-tetrahydro-1H,3H-oxepino [3',4':6,7]indolizino[1,2-b]quinoleine-3,15-dione;

(5R)-5-ethyl-9,10-difluoro-5-hydroxy-12-(3,3,3-trifluoropropyl)-4,5,13,15-tetrahydro-1H,3H-oxepino[3',4':6,7]indolizino[1,2-b]quinoleine-3,15-dione;

(5R)-5-ethyl-9,10-difluoro-5-hydroxy-12-isopentyl-4,5,13,15-tetrahydro-1H,3H-oxepino [3',4':6,7]indolizino[1,2-b]quinoleine-3,15-dione;

(5R)-5-ethyl-9,10-difluoro-5-hydroxy-12-pentyl-4,5,13,15-tetrahydro-1H,3H-oxepino[3',4':6,7]indolizino[1,2-b]quinoleine-3,15-dione;

(5R)-5-ethyl-9,10-difluoro-5-hydroxy-12-phenethyl-4,5,13,15-tetrahydro-1H,3H-oxepino [3',4':6,7]indolizino[1,2-b]quinoleine-3,15-dione;

(5R)-12-(2-cyclohexylethyl)-5-ethyl-9,10-difluoro-5-hydroxy-4,5,13,15-tetrahydro-1H,3H-oxepino[3',4':6,7]indolizino[1,2-b]quinoleine-3,15-dione;

(5R)-12-(3,3-dimethylbutyl)-5-ethyl-9,10-difluoro-5-hydroxy-4,5,13,15-tetrahydro-1H,3H-oxepino[3',4':6,7]indolizino[1,2-b]quinoleine-3,15-dione;

(5R)-5-ethyl-9,11-difluoro-5-hydroxy-12-propyl-4,5,13,15-tetrahydro-1H,3H-oxepino [3',4':6,7]indolizino[1,2-b]quinoleine-3,15-dione;

(5R)-5-ethyl-9,11-difluoro-5-hydroxy-12-(3,3,3-trifluoropropyl)-4,5,13,15-tetrahydro-1H,3H-oxepino[3',4':6,7]indolizino[1,2-b]quinoleine-3,15-dione;

(5R)-5-ethyl-9,11-difluoro-5-hydroxy-12-isopentyl-4,5,13,15-tetrahydro-1H,3H-oxepino [3',4':6,7]indolizino[1,2-b]quinoleine-3,15-dione;

(5R)-5-ethyl-9,11-difluoro-5-hydroxy-12-pentyl-4,5,13,15-tetrahydro-1H,3H-oxepino [3',4':6,7]indolizino[1,2-b]quinoleine-3,15-dione;

(5R)-5-ethyl-9,11-difluoro-5-hydroxy-12-phenethyl-4,5,13,15-tetrahydro-1H,3H-oxepino [3',4':6,7]indolizino[1,2-b]quinoleine-3,15-dione;

(5R)-12-(2-cyclohexylethyl)-5-ethyl-9,11-difluoro-5-hydroxy-4,5,13,15-tetrahydro-1H,3H-oxepino[3',4':6,7]indolizino[1,2-b]quinoleine-3,15-dione;

(5R)-12-(3,3-dimethylbutyl)-5-ethyl-9,11-difluoro-5-hydroxy-4,5,13,15-tetrahydro-1H,3H-oxepino[3',4':6,7]indolizino[1,2-b]quinoleine-3,15-dione;

(5R)-12-chloro-5-ethyl-5-hydroxy-4,5,13,15-tetrahydro-1H,3H-oxepino[3',4':6,7]indolizino[1,2-b]quinoleine-3,15-dione;

(5R)-5-ethyl-5-hydroxy-12-hydroxymethyl-4,5,13,15-tetrahydro-1H,3H-oxepino [3',4':6,7]indolizino[1,2-b]quinoleine-3,15-dione;

(5R)-5-ethyl-9-fluoro-5-hydroxy-12-isobutyl-4,5,13,15-tetrahydro-1H,3H-oxepino [3',4':6,7]indolizino[1,2-b]quinoleine-3,15-dione;

(5R)-5-ethyl-9-fluoro-5-hydroxy-12-neopentyl-4,5,13,15-tetrahydro-1H,3H-oxepino [3',4':6,7]indolizino[1,2-b]quinoleine-3,15-dione;

(5R)-5-ethyl-9-fluoro-12-(3-fluorophenyl)-5-hydroxy-4,5,13,15-tetrahydro-1H,3H-oxepino [3',4':6,7]indolizino[1,2-b]quinoleine-3,15-dione;

(5R)-5-ethyl-9-fluoro-5-hydroxy-12-(4-trifluoromethylphenyl)-4,5,13,15-tetrahydro-1H,3H-oxepino[3',4':6,7]indolizino[1,2-b]quinoleine-3,15-dione;

(5R)-12-[4-(tert-butyl)phenyl]-5-ethyl-9-fluoro-5-hydroxy-4,5,13,15-tetrahydro-1H,3H-oxepino[3',4':6,7]indolizino [1,2-b]quinoleine-3,15-dione;

(5R)-5-ethyl-9,11-difluoro-5-hydroxy-12-propyl-4,5,13,15-tetrahydro-1H,3H-oxepino [3',4':6,7]indolizino[1,2-b]quinoleine-3,15-dione;

(5R)-12-(2-ethoxyethyl)-5-ethyl-9,11-difluoro-5-hydroxy-4,5,13,15-tetrahydro-1H,3H-oxepino [3',4':6,7]indolizino [1,2-b]quinoleine-3,15-dione;

(5R)-5-ethyl-9,10,11-trifluoro-5-hydroxy-4,5,13,15-tetrahydro-1H,3H-oxepino [3',4':6,7]indolizino[1,2-b]quinoleine-3,15-dione;

or the salts thereof.

By halo is meant in the present Application, fluoro, chloro, bromo or iodo, and preferably chloro, fluoro or bromo. By lower alkyl radical is a linear or branched alkyl radical containing 1 to 6 carbon atoms carbone such methyl, ethyl, propyl, isopropyl, butyl, isobutyl, sec-butyl and tert-butyl, pentyl, isopentyl, neopentyl, hexyl or isohexyl. Among the alkyl radicals containing 1 to 12 carbon atoms, the above lower alkyl radicals may be cited as well as heptyl, octyl, nonyl or decyl radicals. The lower alkoxy radicals may correspond to the lower alkyl radicals as mentioned above such as methoxy, ethoxy, propyloxy, isopropyloxy or linear, sec- or tert-butoxy.

The term cycloalkyl designates a ring with 3 to 7 carbons, such as for example the cyclopropyl, cyclobutyl, cyclopentyl or cyclohexyl groups. The term lower cycloalkyl alkyl refers to radicals cycloalkyl and lower alkyl as mentioned above such as for exemple cyclohexyl methyl, cyclohexyl ethyl. The term aryl designates a mono-, di- or tricyclic hydrocarbon compound with at least one aromatic ring, each ring containing a maximum of 7 members, such as for example phenyl, naphthyl, anthracyl, biphenyl or indenyl. The term lower aryl alkyl designates radicals in which the radicals aryl and lower alkyl respectively are as defined above such as for exemple benzyl, phenethyl or naphtylmethyl.

The term lower hydroxy alkyl refers to radicals in which the alkyl chain may be linear or branched with 1 to 6 carbon atoms. The terms lower alkyl amino and di(lower alkyl) amino preferably designate the radicals in which the alkyl radicals are as defined above such as for exemple methylamino, ethylamino, dimethylamino, diethylamino or (methyl)(ethyl)amino.

The invention relates in particular to the compounds of general formula (II$_A$)

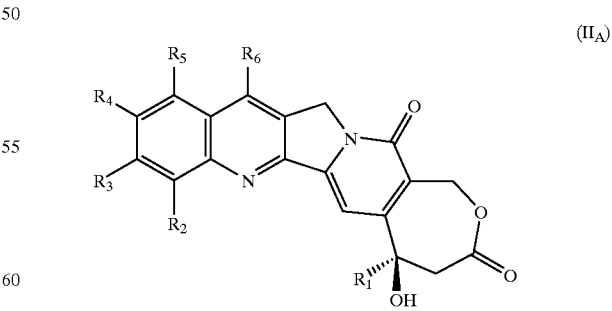

(II$_A$)

in which $R_1$ represents a lower alkyl radical;

$R_2$, $R_3$, $R_4$ and $R_5$ represent, independently, H, a halogen atom or —OSO$_2$R$_{10}$;

R₆ represents H, a linear or branched alkyl radical containing 1 to 12 carbon atoms optionnally substituted by one or more halo radicals indentical or different, lower hydroxy alkyl, lower alkoxy lower alkyl, a cycloalkyl, lower cycloalkyl alkyl, nitro, halo, —(CH₂)ₘSiR₇R₈R₉ radical, or an aryl substituted or non substituted or lower aryl alkyl radical substituted or non substituted on the aryl group, the substituents of the aryl groups being identical or different and selected from: a lower alkyl, a hydroxy group, halo, amino, lower alkyl amino, di(lower alkyl) amino, CF₃ or OCF₃;

R₇, R₈ and R₉ represent, independently, a lower alkyl radical;

R₁₀ represents a lower alkyl radical optionnally substituted by one or more halo radicals identical or different, or an aryl optionnally susbtituted by one or more lower alkyl radicals identical or different;

m is an integer comprised between 0 and 6;

and characterized in that at least one of the radicals R₂, R₃, R₄ or R₅ represents —OSO₂R₁₀, and/or R₆ represents a linear or branched alkyl radical containing 7 à 12 carbon atoms, —(CH₂)ₘSiR₇R₈R₉, or an aryle group substituted by one or more substituents indentical or different and selected from di(lower alkyl)amino and OCF₃, and/or R₂ represents halo, or the salts thereof.

Preferred compounds of the invention are those for which R₁ represents an ethyl radical, as well as those for which R₃ represents halo and in particular fluoro.

The preferred compounds of formula II_A correspond to the following formulae:

(5R)-5-ethyl-8-fluoro-5-hydroxy-4,5,13,15-tetrahydro-1H,3H-oxepino[3',4':6,7]indolizino[1,2-b]quinoleine-3,15-dione;

(5R)-5-ethyl-9,10-difluoro-5-hydroxy-12-(2-trimethylsilylethyl)-4,5,13,15-tetrahydro-1H,3H-oxepino[3',4':6,7]indolizino[1,2-b]quinoleine-3,15-dione;

(5R)-5-ethyl-5-hydroxy-12-(2-trimethylsilylethyl)-4,5,13,15-tetrahydro-1H,3H-oxepino [3',4':6,7]indolizino[1,2-b]quinoleine-3,15-dione;

(5R)-12-decyl-5-ethyl-9-fluoro-5-hydroxy-4,5,13,15-tetrahydro-1H,3H-oxepino [3',4':6,7]indolizino[1,2-b]quinoleine-3,15-dione;

(5R)-12-decyl-5-ethyl-9,10-difluoro-5-hydroxy-4,5,13,15-tetrahydro-1H,3H-oxepino [3',4':6,7]indolizino[1,2-b]quinoleine-3,15-dione;

(5R)-12-decyl-5-ethyl-9,11-difluoro-5-hydroxy-4,5,13,15-tetrahydro-1H,3H-oxepino [3',4':6,7]indolizino[1,2-b]quinoleine-3,15-dione;

(5R)-5-ethyl-9-fluoro-5-hydroxy-12-(4-trifluoromethoxyphenyl)-4,5,13,15-tetrahydro-1H,3H-oxepino[3',4':6,7]indolizino[1,2-b]quinoleine-3,15-dione;

(5R)-12-(4-dimethylaminophenyl)-5-ethyl-9-fluoro-5-hydroxy-4,5,13,15-tetrahydro-1H,3H-oxepino[3',4':6,7]indolizino[1,2-b]quinoleine-3,15-dione;

(5R)-5-ethyl-9-fluoro-5-hydroxy-3,15-dioxo-4,5,13,15-tetrahydro-1H,3H-oxepino [3',4':6,7]indolizino[1,2-b]quinolein-10-yl trifluorometanesulfonate, or the salts thereof, and in particular to the following formulae:

(5R)-5-ethyl-9,10-difluoro-5-hydroxy-12-(2-trimethylsilylethyl)-4,5,13,15-tetrahydro-1H,3H-oxepino[3',4':6,7]indolizino[1,2-b]quinoleine-3,15-dione;

(5R)-5-ethyl-5-hydroxy-12-(2-trimethylsilylethyl)-4,5,13,15-tetrahydro-1H,3H-oxepino [3',4':6,7]indolizino[1,2-b]quinoleine-3,15-dione.

The invention relates in particular also to compounds of the formula I as defined above and corresponding to the following formulae:

(5R)-5-ethyl-11-fluoro-5-hydroxy-4,5,13,15-tetrahydro-1H,3H-oxepino[3',4':6,7]indolizino[1,2-b]quinoleine-3,15-dione;

(5R)-5-ethyl-9-fluoro-5-hydroxy-4,5,13,15-tetrahydro-1H,3H-oxepino[3',4':6,7]indolizino[1,2-b]quinoleine-3,15-dione;

(5R)-12-benzyl-5-ethyl-5-hydroxy-4,5,13,15-tetrahydro-1H,3H-oxepino[3',4':6,7]indolizino[1,2-b]quinoleine-3,15-dione;

(5R)-12-butyl-5-ethyl-5-hydroxy-4,5,13,15-tetrahydro-1H,3H-oxepino[3',4':6,7]indolizino[1,2-b]quinoleine-3,15-dione;

(5R)-5,12-diethyl-5-hydroxy-4,5,13,15-tetrahydro-1H,3H-oxepino[3',4':6,7]indolizino[1,2-b]quinoleine-3,15-dione;

(5R)-5-ethyl-5-hydroxy-12-phenyl-4,5,13,15-tetrahydro-1H,3H-oxepino[3',4':6,7]indolizino[1,2-b]quinoleine-3,15-dione;

(5R)-12-cyclohexyl-5-ethyl-5-hydroxy-4,5,13,15-tetrahydro-1H,3H-oxepino[3',4':6,7]indolizino[1,2-b]quinoleine-3,15-dione;

(5R)-5-ethyl-5-hydroxy-12-(4-methylphenyl)-4,5,13,15-tetrahydro-1H,3H-oxepino [3',4':6,7]indolizino[1,2-b]quinoleine-3,15-dione;

(5R)-10-chloro-5-ethyl-12-(2-fluorophenyl)-5-hydroxy-4,5,13,15-tetrahydro-1H,3H-oxepino[3',4':6,7]indolizino[1,2-b]quinoleine-3,15-dione;

(5R)-5-ethyl-9,10-difluoro-5-hydroxy-12-phenyl-4,5,13,15-tetrahydro-1H,3H-oxepino [3',4':6,7]indolizino[1,2-b]quinoleine-3,15-dione;

(5R)-5-ethyl-9-fluoro-5-hydroxy-12-phenyl-4,5,13,15-tetrahydro-1H,3H-oxepino [3',4':6,7]indolizino[1,2-b]quinoleine-3,15-dione;

(5R)-12-butyl-5-ethyl-9,10-difluoro-5-hydroxy-4,5,13,15-tetrahydro-1H,3H-oxepino [3',4':6,7]indolizino[1,2-b]quinoleine-3,15-dione;

(5R)-12-benzyl-5-ethyl-9,10-difluoro-5-hydroxy-4,5,13,15-tetrahydro-1H,3H-oxepino [3',4':6,7]indolizino[1,2-b]quinoleine-3,15-dione;

(5R)-5-ethyl-9,10-difluoro-5-hydroxy-12-propyl-4,5,13,15-tetrahydro-1H,3H-oxepino [3',4':6,7]indolizino[1,2-b]quinoleine-3,15-dione;

(5R)-5,12-diethyl-9,10-difluoro-5-hydroxy-4,5,13,15-tetrahydro-1H,3H-oxepino [3',4':6,7]indolizino[1,2-b]quinoleine-3,15-dione;

(5R)-5-ethyl-9,11-difluoro-5-hydroxy-4,5; 13,15-tetrahydro-1H,3H-oxepino[3',4':6,7]indolizino[1,2-b]quinoleine-3,15-dione;

(5R)-12-butyl-5-ethyl-9,11-difluoro-5-hydroxy-4,5,13,15-tetrahydro-1H,3H-oxepino [3',4':6,7]indolizino[1,2-b]quinoleine-3,15-dione;

(5R)-5,12-diethyl-9,11-difluoro-5-hydroxy-4,5,13,15-tetrahydro-1H,3H-oxepino [3',4':6,7]indolizino[1,2-b]quinoleine-3,15-dione;

(5R)-5-ethyl-5-hydroxy-12-propyl-4,5,13,15-tetrahydro-1H,3H-oxepino [3',4':6,7]indolizino[1,2-b]quinoleine-3,15-dione;

(5R)-12-butyl-5-ethyl-9-fluoro-5-hydroxy-4,5,13,15-tetrahydro-1H,3H-oxepino [3',4':6,7]indolizino[1,2-b]quinoleine-3,15-dione;

(5R)-5,12-diethyl-9-fluoro-5-hydroxy-4,5,13,15-tetrahydro-1H,3H-oxepino [3',4':6,7]indolizino[1,2-b]quinoleine-3,15-dione;

(5R)-5-ethyl-5-hydroxy-12-isopentyl-4,5,13,15-tetrahydro-1H,3H-oxepino [3',4':6,7]indolizino[1,2-b]quinoleine-3,15-dione;

(5R)-5-ethyl-9-fluoro-12-(4-fluorophenyl)-5-hydroxy-4,5,13,15-tetrahydro-1H,3H-oxepino [3',4':6,7]indolizino[1,2-b]quinoleine-3,15-dione;

(5R)-12-(3,5-difluorophenyl)-5-ethyl-9-fluoro-5-hydroxy-4,5,13,15-tetrahydro-1H,3H-oxepino [3',4':6,7]indolizino[1,2-b]quinoleine-3,15-dione;

(5R)-5-ethyl-9-fluoro-5-hydroxy-12-phenethyl-4,5,13,15-tetrahydro-1H,3H-oxepino [3',4':6,7]indolizino[1,2-b]quinoleine-3,15-dione;

(5R)-12-chloro-5-ethyl-5-hydroxy-4,5,13,15-tetrahydro-1H,3H-oxepino[3',4':6,7]indolizino[1,2-b]quinoleine-3,15-dione;

(5R)-5-ethyl-5-hydroxy-12-hydroxymethyl-4,5,13,15-tetrahydro-1H,3H-oxepino [3',4':6,7]indolizino[1,2-b]quinoleine-3,15-dione;

(5R)-5-ethyl-9-fluoro-5-hydroxy-12-isobutyl-4,5,13,15-tetrahydro-1H,3H-oxepino [3',4':6,7]indolizino[1,2-b]quinoleine-3,15-dione;

(5R)-5-ethyl-9-fluoro-5-hydroxy-12-neopentyl-4,5,13,15-tetrahydro-1H,3H-oxepino [3',4':6,7]indolizino[1,2-b]quinoleine-3,15-dione;

(5R)-5-ethyl-9-fluoro-12-(3-fluorophenyl)-5-hydroxy-4,5,13,15-tetrahydro-1H,3H-oxepino [3',4':6,7]indolizino[1,2-b]quinoleine-3,15-dione;

(5R)-5-ethyl-9-fluoro-5-hydroxy-12-(4-trifluoromethylphenyl)-4,5,13,15-tetrahydro-1H,3H-oxepino[3',4':6,7]indolizino[1,2-b]quinoleine-3,15-dione;

(5R)-12-[4-(tert-butyl)phenyl]-5-ethyl-9-fluoro-5-hydroxy-4,5,13,15-tetrahydro-1H,3H-oxepino[3',4':6,7]indolizino[1,2-b]quinoleine-3,15-dione;

(5R)-5-ethyl-9,11-difluoro-5-hydroxy-12-propyl-4,5,13,15-tetrahydro-1H,3H-oxepino [3',4':6,7]indolizino[1,2-b]quinoleine-3,15-dione;

(5R)-12-(2-ethoxyethyl)-5-ethyl-9,11-difluoro-5-hydroxy-4,5,13,15-tetrahydro-1H,3H-oxepino [3',4':6,7]indolizino[1,2-b]quinoleine-3,15-dione;

(5R)-5-ethyl-9,10,11-trifluoro-5-hydroxy-4,5,13,15-tetrahydro-1H,3H-oxepino [3',4':6,7]indolizino[1,2-b]quinoleine-3,15-dione;

or the salts thereof, and more particularly to the following formulae:

(5R)-5-ethyl-9-fluoro-5-hydroxy-4,5,13,15-tetrahydro-1H,3H-oxepino[3',4':6,7]indolizino[1,2-b]quinoleine-3,15-dione;

(5R)-5,12-diethyl-9,10-difluoro-5-hydroxy-4,5,13,15-tetrahydro-1H,3H-oxepino [3',4':6,7]indolizino[1,2-b]quinoleine-3,15-dione;

(5R)-5-ethyl-9,11-difluoro-5-hydroxy-4,5,13,15-tetrahydro-1H,3H-oxepino[3',4':6,7]indolizino[1,2-b]quinoleine-3,15-dione;

(5R)-5,12-diethyl-9-fluoro-5-hydroxy-4,5,13,15-tetrahydro-1H,3H-oxepino[3',4':6,7]indolizino[1,2-b]quinoleine-3,15-dione;

(5R)-5-ethyl-9-fluoro-12-(4-fluorophenyl)-5-hydroxy-4,5,13,15-tetrahydro-1H,3H-oxepino[3',4':6,7]indolizino[1,2-b]quinoleine-3,15-dione;

(5R)-12-(3,5-difluorophenyl)-5-ethyl-9-fluoro-5-hydroxy-4,5,13,15-tetrahydro-1H,3H-oxepino [3',4':6,7]indolizino[1,2-b]quinoleine-3,15-dione;

(5R)-5-ethyl-9-fluoro-5-hydroxy-12-phenethyl-4,5,13,15-tetrahydro-1H,3H-oxepino [3',4':6,7]indolizino[1,2-b]quinoleine-3,15-dione;

(5R)-12-chloro-5-ethyl-5-hydroxy-4,5,13,15-tetrahydro-1H,3H-oxepino [3',4':6,7]indolizino[1,2-b]quinoleine-3,15-dione;

(5R)-5-ethyl-9-fluoro-12-(3-fluorophenyl)-5-hydroxy-4,5,13,15-tetrahydro-1H,3H-oxepino [3',4':6,7]indolizino[1,2-b]quinoleine-3,15-dione;

(5R)-5-ethyl-9-fluoro-5-hydroxy-12-(4-trifluoromethylphenyl)-4,5,13,15-tetrahydro-1H,3H-oxepino[3',4':6,7]indolizino[1,2-b]quinoleine-3,15-dione;

(5R)-5-ethyl-9,11-difluoro-5-hydroxy-12-propyl-4,5,13,15-tetrahydro-1H,3H-oxepino [3',4':6,7]indolizino[1,2-b]quinoleine-3,15-dione;

(5R)-12-(2-ethoxyethyl)-5-ethyl-9,11-difluoro-5-hydroxy-4,5,13,15-tetrahydro-1H,3H-oxepino [3',4':6,7]indolizino[1,2-b]quinoleine-3,15-dione;

or the salts thereof.

The invention relates in particular also to compounds of formula I as above defined and corresponding to the following formulae:

(5R)-5-ethyl-9-fluoro-5-hydroxy-4,5,13,15-tetrahydro-1H,3H-oxepino[3',4':6,7]indolizino[1,2-b]quinoleine-3,15-dione;

(5R)-5-ethyl-9,10-difluoro-5-hydroxy-12-phenyl-4,5,13,15-tetrahydro-1H,3H-oxepino [3',4':6,7]indolizino[1,2-b]quinoleine-3,15-dione;

(5R)-5-ethyl-9-fluoro-5-hydroxy-12-phenyl-4,5,13,15-tetrahydro-1H,3H-oxepino [3',4':6,7]indolizino[1,2-b]quinoleine-3,15-dione;

(5R)-12-butyl-5-ethyl-9,10-difluoro-5-hydroxy-4,5,13,15-tetrahydro-1H,3H-oxepino [3',4':6,7]indolizino[1,2-b]quinoleine-3,15-dione;

(5R)-12-benzyl-5-ethyl-9,10-difluoro-5-hydroxy-4,5,13,15-tetrahydro-1H,3H-oxepino [3',4':6,7]indolizino[1,2-b]quinoleine-3,15-dione;

(5R)-5-ethyl-9,10-difluoro-5-hydroxy-12-propyl-4,5,13,15-tetrahydro-1H,3H-oxepino [3',4':6,7]indolizino[1,2-b]quinoleine-3,15-dione;

(5R)-5,12-diethyl-9,10-difluoro-5-hydroxy-4,5,13,15-tetrahydro-1H,3H-oxepino [3',4':6,7]indolizino[1,2-b]quinoleine-3,15-dione;

(5R)-5-ethyl-9,10-difluoro-5-hydroxy-12-(2-trimethylsilylethyl)-4,5,13,15-tetrahydro-1H,3H-oxepino [3',4':6,7]indolizino[1,2-b]quinoleine-3,15-dione;

(5R)-5-ethyl-9,11-difluoro-5-hydroxy-4,5,13,15-tetrahydro-1H,3H-oxepino [3',4':6,7]indolizino[1,2-b]quinoleine-3,15-dione;

(5R)-12-butyl-5-ethyl-9,11-difluoro-5-hydroxy-4,5,13,15-tetrahydro-1H,3H-oxepino [3',4':6,7]indolizino[1,2-b]quinoleine-3,15-dione;

(5R)-5,12-diethyl-9,11-difluoro-5-hydroxy-4,5,13,15-tetrahydro-1H,3H-oxepino [3',4':6,7]indolizino[1,2-b]quinoleine-3,15-dione;

(5R)-12-butyl-5-ethyl-9-fluoro-5-hydroxy-4,5,13,15-tetrahydro-1H,3H-oxepino [3',4':6,7]indolizino[1,2-b]quinoleine-3,15-dione;

(5R)-5,12-diethyl-9-fluoro-5-hydroxy-4,5,13,15-tetrahydro-1H,3H-oxepino [3',4':6,7]indolizino[1,2-b]quinoleine-3,15-dione;

(5R)-5-ethyl-9-fluoro-12-(4-fluorophenyl)-5-hydroxy-4,5,13,15-tetrahydro-1H,3H-oxepino[3',4':6,7]indolizino[1,2-b]quinoleine-3,15-dione;

(5R)-12-(2,6-difluorophenyl)-5-ethyl-9-fluoro-5-hydroxy-4,5,13,15-tetrahydro-1H,3H-oxepino[3',4':6,7]indolizino[1,2-b]quinoleine-3,15-dione;

(5R)-12-(3,5-difluorophenyl)-5-ethyl-9-fluoro-5-hydroxy-4,5,13,15-tetrahydro-1H,3H-oxepino[3',4':6,7]indolizino[1,2-b]quinoleine-3,15-dione;

(5R)-5-ethyl-9-fluoro-5-hydroxy-12-(3,4,5-trifluorophenyl)-4,5,13,15-tetrahydro-1H,3H-oxepino[3',4':6,7]indolizino[1,2-b]quinoleine-3,15-dione;

(5R)-5-ethyl-9-fluoro-5-hydroxy-12-(2,4,6-trifluorophenyl)-4,5,13,15-tetrahydro-1H,3H-oxepino[3',4':6,7]indolizino[1,2-b]quinoleine-3,15-dione;

(5R)-5-ethyl-9-fluoro-5-hydroxy-12-(2,3,5,6-tetrafluorophenyl)-4,5,13,15-tetrahydro-1H,3H-oxepino[3',4':6,7]indolizino[1,2-b]quinoleine-3,15-dione;

(5R)-5-ethyl-9-fluoro-5-hydroxy-12-(2,3,4,5,6-pentafluorophenyl)-4,5,13,15-tetrahydro-1H,3H-oxepino[3',4':6,7]indolizino[1,2-b]quinoleine-3,15-dione;

(5R)-5-ethyl-9,10-difluoro-12-(4-fluorophenyl)-5-hydroxy-4,5,13,15-tetrahydro-1H,3H-oxepino[3',4':6,7]indolizino[1,2-b]quinoleine-3,15-dione;

(5R)-12-(2,6-difluorophenyl)-5-ethyl-9,10-difluoro-5-hydroxy-4,5,13,15-tetrahydro-1H,3H-oxepino[3',4':6,7]indolizino[1,2-b]quinoleine-3,15-dione;

(5R)-12-(3,5-difluorophenyl)-5-ethyl-9,10-difluoro-5-hydroxy-4,5,13,15-tetrahydro-1H,3H-oxepino[3',4':6,7]indolizino[1,2-b]quinoleine-3,15-dione;

(5R)-5-ethyl-9,10-difluoro-5-hydroxy-12-(3,4,5-trifluorophenyl)-4,5,13,15-tetrahydro-1H,3H-oxepino[3',4':6,7]indolizino[1,2-b]quinoleine-3,15-dione;

(5R)-5-ethyl-9,10-difluoro-5-hydroxy-12-(2,4,6-trifluorophenyl)-4,5,13,15-tetrahydro-1H,3H-oxepino[3',4':6,7]indolizino[1,2-b]quinoleine-3,15-dione;

(5R)-5-ethyl-9,10-difluoro-5-hydroxy-12-(2,3,5,6-tetrafluorophenyl)-4,5,13,15-tetrahydro-1H,3H-oxepino[3',4':6,7]indolizino[1,2-b]quinoleine-3,15-dione;

(5R)-5-ethyl-9,10-difluoro-5-hydroxy-12-(2,3,4,5,6-pentafluorophenyl)-4,5,13,15-tetrahydro-1H,3H-oxepino[3',4':6,7]indolizino[1,2-b]quinoleine-3,15-dione;

(5R)-5-ethyl-9,11-difluoro-12-(4-fluorophenyl)-5-hydroxy-4,5,13,15-tetrahydro-1H,3H-oxepino[3',4':6,7]indolizino[1,2-b]quinoleine-3,15-dione;

(5R)-12-(2,6-difluorophenyl)-5-ethyl-9,11-difluoro-5-hydroxy-4,5,13,15-tetrahydro-1H,3H-oxepino[3',4':6,7]indolizino[1,2-b]quinoleine-3,15-dione;

(5R)-12-(3,5-difluorophenyl)-5-ethyl-9,11-difluoro-5-hydroxy-4,5,13,15-tetrahydro-1H,3H-oxepino[3',4':6,7]indolizino[1,2-b]quinoleine-3,15-dione;

(5R)-5-ethyl-9,11-difluoro-5-hydroxy-12-(3,4,5-trifluorophenyl)-4,5,13,15-tetrahydro-1H,3H-oxepino[3',4':6,7]indolizino[1,2-b]quinoleine-3,15-dione;

(5R)-5-ethyl-9,11-difluoro-5-hydroxy-12-(2,4,6-trifluorophenyl)-4,5,13,15-tetrahydro-1H,3H-oxepino[3',4':6,7]indolizino[1,2-b]quinoleine-3,15-dione;

(5R)-5-ethyl-9,11-difluoro-5-hydroxy-12-(2,3,5,6-tetrafluorophenyl)-4,5,13,15-tetrahydro-1H,3H-oxepino[3',4':6,7]indolizino[1,2-b]quinoleine-3,15-dione;

(5R)-5-ethyl-9,11-difluoro-5-hydroxy-12-(2,3,4,5,6-pentafluorophenyl)-4,5,13,15-tetrahydro-1H,3H-oxepino[3',4':6,7]indolizino[1,2-b]quinoleine-3,15-dione;

(5R)-5-ethyl-9-fluoro-5-hydroxy-12-propyl-4,5,13,15-tetrahydro-1H,3H-oxepino[3',4':6,7]indolizino[1,2-b]quinoleine-3,15-dione;

(5R)-5-ethyl-9-fluoro-5-hydroxy-12-(3,3,3-trifluoropropyl)-4,5,13,15-tetrahydro-1H,3H-oxepino[3',4':6,7]indolizino[1,2-b]quinoleine-3,15-dione;

(5R)-5-ethyl-9-fluoro-5-hydroxy-12-isopentyl-4,5,13,15-tetrahydro-1H,3H-oxepino[3',4':6,7]indolizino[1,2-b]quinoleine-3,15-dione;

(5R)-5-ethyl-9-fluoro-5-hydroxy-12-pentyl-4,5,13,15-tetrahydro-1H,3H-oxepino[3',4':6,7]indolizino[1,2-b]quinoleine-3,15-dione;

(5R)-5-ethyl-9-fluoro-5-hydroxy-12-phenethyl-4,5,13,15-tetrahydro-1H,3H-oxepino[3',4':6,7]indolizino[1,2-b]quinoleine-3,15-dione;

(5R)-12-decyl-5-ethyl-9-fluoro-5-hydroxy-4,5,13,15-tetrahydro-1H,3H-oxepino[3',4':6,7]indolizino[1,2-b]quinoleine-3,15-dione;

(5R)-12-(2-cyclohexylethyl)-5-ethyl-9-fluoro-5-hydroxy-4,5,13,15-tetrahydro-1H,3H-oxepino[3',4':6,7]indolizino[1,2-b]quinoleine-3,15-dione;

(5R)-12-(3,3-dimethylbutyl)-5-ethyl-9-fluoro-5-hydroxy-4,5,13,15-tetrahydro-1H,3H-oxepino[3',4':6,7]indolizino[1,2-b]quinoleine-3,15-dione;

(5R)-5-ethyl-9,10-difluoro-5-hydroxy-12-propyl-4,5,13,15-tetrahydro-1H,3H-oxepino[3',4':6,7]indolizino[1,2-b]quinoleine-3,15-dione;

(5R)-5-ethyl-9,10-difluoro-5-hydroxy-12-(3,3,3-trifluoropropyl)-4,5,13,15-tetrahydro-1H,3H-oxepino[3',4':6,7]indolizino[1,2-b]quinoleine-3,15-dione;

(5R)-5-ethyl-9,10-difluoro-5-hydroxy-12-isopentyl-4,5,13,15-tetrahydro-1H,3H-oxepino[3',4':6,7]indolizino[1,2-b]quinoleine-3,15-dione;

(5R)-5-ethyl-9,10-difluoro-5-hydroxy-12-pentyl-4,5,13,15-tetrahydro-1H,3H-oxepino[3',4':6,7]indolizino[1,2-b]quinoleine-3,15-dione;

(5R)-5-ethyl-9,10-difluoro-5-hydroxy-12-phenethyl-4,5,13,15-tetrahydro-1H,3H-oxepino[3',4':6,7]indolizino[1,2-b]quinoleine-3,15-dione;

(5R)-12-decyl-5-ethyl-9,10-difluoro-5-hydroxy-4,5,13,15-tetrahydro-1H,3H-oxepino[3',4':6,7]indolizino[1,2-b]quinoleine-3,15-dione;

(5R)-12-(2-cyclohexylethyl)-5-ethyl-9,10-difluoro-5-hydroxy-4,5,13,15-tetrahydro-1H,3H-oxepino[3',4':6,7]indolizino[1,2-b]quinoleine-3,15-dione;

(5R)-12-(3,3-dimethylbutyl)-5-ethyl-9,10-difluoro-5-hydroxy-4,5,13,15-tetrahydro-1H,3H-oxepino[3',4':6,7]indolizino[1,2-b]quinoleine-3,15-dione;

(5R)-5-ethyl-9,11-difluoro-5-hydroxy-12-propyl-4,5,13,15-tetrahydro-1H,3H-oxepino[3',4':6,7]indolizino[1,2-b]quinoleine-3,15-dione;

(5R)-5-ethyl-9,11-difluoro-5-hydroxy-12-(3,3,3-trifluoropropyl)-4,5,13,15-tetrahydro-1H,3H-oxepino[3',4':6,7]indolizino[1,2-b]quinoleine-3,15-dione;

(5R)-5-ethyl-9,11-difluoro-5-hydroxy-12-isopentyl-4,5,13,15-tetrahydro-1H,3H-oxepino[3',4':6,7]indolizino[1,2-b]quinoleine-3,15-dione;

(5R)-5-ethyl-9,11-difluoro-5-hydroxy-12-pentyl-4,5,13,15-tetrahydro-1H,3H-oxepino[3',4':6,7]indolizino[1,2-b]quinoleine-3,15-dione;

(5R)-5-ethyl-9,11-difluoro-5-hydroxy-12-phenethyl-4,5,13,15-tetrahydro-1H,3H-oxepino[3',4':6,7]indolizino[1,2-b]quinoleine-3,15-dione;

(5R)-12-decyl-5-ethyl-9,11-difluoro-5-hydroxy-4,5,13,15-tetrahydro-1H,3H-oxepino[3',4':6,7]indolizino[1,2-b]quinoleine-3,15-dione;

(5R)-12-(2-cyclohexylethyl)-5-ethyl-9,11-difluoro-5-hydroxy-4,5,13,15-tetrahydro-1H,3H-oxepino[3',4':6,7]indolizino[1,2-b]quinoleine-3,15-dione;

(5R)-12-(3,3-dimethylbutyl)-5-ethyl-9,11-difluoro-5-hydroxy-4,5,13,15-tetrahydro-1H,3H-oxepino[3',4':6,7]indolizino[1,2-b]quinoleine-3,15-dione;

(5R)-12-chloro-5-ethyl-5-hydroxy-4,5,13,15-tetrahydro-1H,3H-oxepino[3',4':6,7]indolizino[1,2-b]quinoleine-3,15-dione;

(5R)-5-ethyl-5-hydroxy-12-hydroxymethyl-4,5,13,15-tetrahydro-1H,3H-oxepino[3',4':6,7]indolizino[1,2-b]quinoleine-3,15-dione;

(5R)-5-ethyl-9-fluoro-5-hydroxy-12-isobutyl-4,5,13,15-tetrahydro-1H,3H-oxepino [3',4':6,7]indolizino[1,2-b]quinoleine-3,15-dione;
(5R)-5-ethyl-9-fluoro-5-hydroxy-12-neopentyl-4,5,13,15-tetrahydro-1H,3H-oxepino [3',4':6,7]indolizino[1,2-b]quinoleine-3,15-dione;
(5R)-5-ethyl-9-fluoro-12-(3-fluorophenyl)-5-hydroxy-4,5,13,15-tetrahydro-1H,3H-oxepino [3',4':6,7]indolizino[1,2-b]quinoleine-3,15-dione;
(5R)-5-ethyl-9-fluoro-5-hydroxy-12-(4-trifluoromethyphenyl)-4,5,13,15-tetrahydro-1H,3H-oxepino[3',4':6,7]indolizino[1,2-b]quinoleine-3,15-dione;
(5R)-5-ethyl-9-fluoro-5-hydroxy-12-(4-trifluoromethoxyphenyl)-4,5,13,15-tetrahydro-1H,3H-oxepino[3',4':6,7]indolizino[1,2-b]quinoleine-3,15-dione;
(5R)-12-(4-dimethylaminophenyl)-5-ethyl-9-fluoro-5-hydroxy-4,5,13,15-tetrahydro-1H,3H-oxepino[3',4':6,7]indolizino[1,2-b]quinoleine-3,15-dione;
(5R)-12-[4-(tert-butyl)phenyl]-5-ethyl-9-fluoro-5-hydroxy-4,5,13,15-tetrahydro-1H,3H-oxepino[3',4':6,7]indolizino[1,2-b]quinoleine-3,15-dione;
(5R)-5-ethyl-9,11-difluoro-5-hydroxy-12-propyl-4,5,13,15-tetrahydro-1H,3H-oxepino [3',4':6,7]indolizino[1,2-b]quinoleine-3,15-dione;
(5R)-12-(2-ethoxyethyl)-5-ethyl-9,11-difluoro-5-hydroxy-4,5,13,15-tetrahydro-1H,3H-oxepino [3',4':6,7]indolizino[1,2-b]quinoleine-3,15-dione;
(5R)-5-ethyl-9,10,11-trifluoro-5-hydroxy-4,5,13,15-tetrahydro-1H,3H-oxepino [3',4':6,7]indolizino[1,2-b]quinoleine-3,15-dione;
(5R)-5-ethyl-9-fluoro-5-hydroxy-3,15-dioxo-4,5,13,15-tetrahydro-1H,3H-oxepino [3',4':6,7]indolizino[1,2-b]quinolein-10-yl trifluorometanesulfonate;

or the salts thereof.

The compounds of general formula (I) can be prepared in the following manner:
the compound of formula M

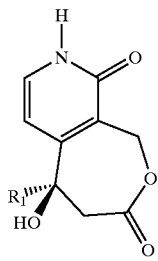

in which $R_1$ has the meaning indicated above, is coupled with a compound of formula N

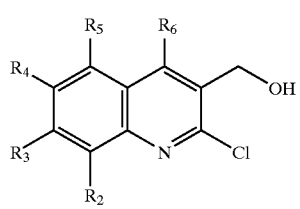

in which $R_2$, $R_3$, $R_4$, $R_5$ and $R_6$ have the meaning indicated above, to produce the compound of formula

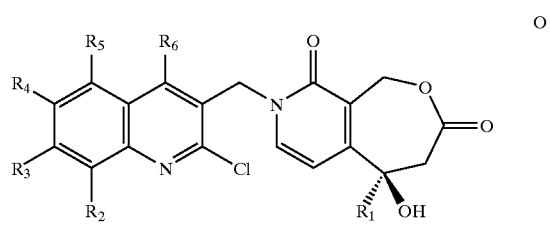

in which $R_2$, $R_3$, $R_4$, $R_5$ and $R_6$ have the meaning indicated above.

compound O is then cyclized to produce the compound of formula (I).

The formation of compounds O starting from the compounds of general formulae M and N is carried out by a treatment known to a person skilled in the art under the name of Mitsunobu's reaction (refer to Mitsunobu, O. et al. *Synthesis*, p. 1 (1981)). The hydroxyl function of compound N is displaced by a nucleophile such as compound M or a deprotonated derivative thereof, by a treatment with a phosphine, for example triphenylphosphine, and an azodicarboxylate derivative, for example diethyl or diisopropyl azodicarboxylate, in an aprotic solvent such as, for example, tetrahydrofuran or N,N-dimethylformamide. The cyclization of compounds O to produce the compounds of formula (I) is preferably carried out in the presence of a palladium catalyst (for example palladium diacetate) under basic conditions (provided for example by an alkaline acetate optionally combined with a phase transfer agent, such as, for example, tetrabutylammonium bromide), in an aprotic solvent such as acetonitrile or N,N-dimethylformamide, at a temperature comprised between 50° C. and 120° C. (R. Grigg et al., *Tetrahedron* 46, page 4003 (1990)).

The invention also offers, as a new industrial product, a compound of general formula M as defined previously. Preferably, $R_1$ represents an ethyl radical. This product M can be used for the manufacture of medicaments.

The compound of formula M is prepared according to a new process which is part of the invention and includes the following successive stages:
a racemic ester represented below

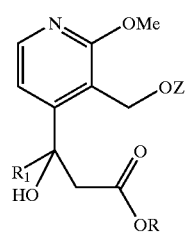

in which $R_1$ has the meaning indicated above, R is a lower alkyl and Z a protective group of the alcohol function (for its preparation, see in particular the Patent Application WO 97/00876) is converted to the corresponding carboxylic acid;
this compound is then subjected to an operation which separates the enantiomers, known to the person skilled in the art under the name of resolution (cf Jacques, et al., "*Enantiomers, Racemates and Resolution*", 2nd edition, Wiley, New-York, 1991), and which allows an enantiomerically enriched compound of general formula

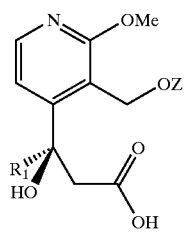

to be obtained, in which $R_1$ and Z have the meaning indicated above;

the alcohol function of the compound of general formula A is then deprotected to produce the product of general formula

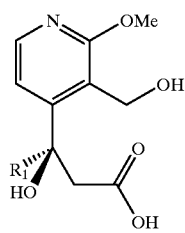

in which $R_1$ has the meaning indicated above, the compound of general formula B is cyclized in order to obtain the compound of general formula

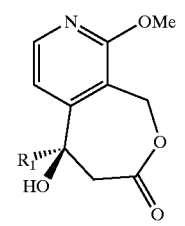

in which $R_1$ has the meaning indicated above, finally, the methoxy group of the compound of general formula C is converted to carbonyl in order to obtain a compound of general formula

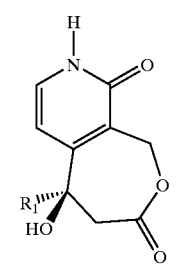

in which $R_1$ has the meaning indicated above.

In the particular case where $R_1$ represents an ethyl group, R represents a tert-butyl and Z represents a benzyl group, the compound of formula M is synthesized according to the process constituted by the following successive stages:

the racemic t-butyl ester represented below (for its preparation, refer in particular to the Patent Application WO 97/00876)

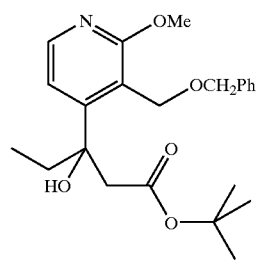

is treated with trifluoro acetic acid for 18 hours at ambient temperature to produce the corresponding carboxylic acid;

the quinidine salt of 3-(3-benzyloxymethyl-2-methoxy-4-pyridyl)-3-hydroxypentanoic acid is heated at a temperature greater than 30° C., and preferably approximately 50° C. in isopropyl alcohol, before the reaction medium is allowed to cool down to ambient temperature so that the (+) enantiomer salt of 3-(3-benzyloxymethyl-2-methoxy-4-pyridyl)-3-hydroxy-pentanoic acid crystallizes whilst the (−) isomer salt, the anion of which is represented below, remains in solution

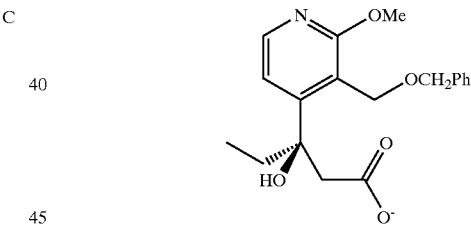

the solution in isopropyl alcohol of the (−) enantiomer salt of 3-(3-benzyloxymethyl-2-methoxy-4-pyridyl)-3-hydroxy-pentanoic acid is concentrated and treated with hydrochloric acid to produce the compound of formula

A′ compound A′ is then put in contact with palladium in the presence of a hydrogen source to produce the debenzylated product of formula B′

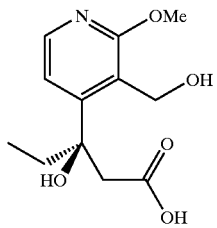

B' the compound of formula B' is then cyclized in order to obtain the compound of formula C'

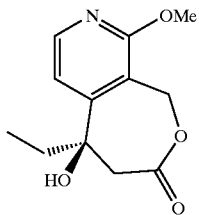

C' finally, the methoxy group of the compound of formula C' is converted to carbonyl is converted in order to obtain (+)-5-ethyl-5-hydroxy-1,3,4,5,8,9-hexahydrooxepino[3,4-c]pyridin-3,9-dione (or (+)-EHHOPD) represented below.

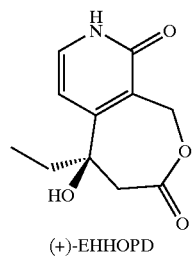

(+)-EHHOPD

For the process described above, the reaction leading from the compound of formula A' to the compound of formula B' preferably takes place in methanol, and preferably by heating the reaction medium to about 40° C. after the addition of ammonium formate. The cyclization of the compound of formula B' to produce compound C' can be carried out in THF, preferably at a temperature of about 50° C., while the reaction will preferably be carried out at ambient temperature with acetonitrile as solvent in the reaction leading from the compound of formula C' to (+)-EHHOPD.

The compounds of formula (I) in which at least one of the radicals $R_2$, $R_3$, $R_4$ or $R_5$ represent a sulfonate (such as mesylate, triflate or tosylate), can be obtained according to a process characterized in that the corresponding hydroxy compound is treated in an anhydrous aprotic solvent with a sulfonyling agent in presence of a base. The aprotic solvent may be dichloromethane or N,N-dimethylformamide, the sulfonyling agent methanesulfonyle chloride, triflic anhydride, N-phenyltriflimide or p-toluene sulfonyl chloride, and the base triethylamine, pyridine or sodium hydride. The sulfonate group may also be introduced in the intermediate compounds.

The compounds of formula N, in which and $R_6$ is a hydrogen atom and $R_2$, $R_3$, $R_4$ and $R_5$ have the meaning indicated above, can be obtained from anilines of formula

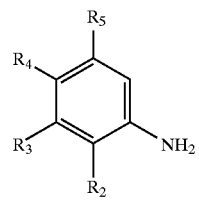

P in which $R_2$, $R_3$, $R_4$ and $R_5$ have the meaning indicated above, according to the following process: an aniline of formula P is N-acetylated by treatment with an acetylating agent such as, for example, acetic anhydride. The acetanilide thus obtained is treated at a temperature comprised between 50° C. and 100° C., preferably about 75° C., with a reagent known to a person skilled in the art under the name Vilsmeyer's reagent (obtained by the action of phosphoryl oxychloride on N,N-dimethylformamide at a temperature comprised between 0° C. and 10° C.) to produce the corresponding 2-chloro-3-quinolinecarbaldehyde (for example, refer to Meth-Cohn et al. *J. Chem. Soc., Perkin Trans. I* p. 1520 (1981); Meth-Cohn et al. *J. Chem. Soc., Perkin Trans. I* p. 2509 (1981); and Nakasimhan et al. *J. Am. Chem. Soc.*, 112 p. 4431 (1990)). This intermediate is easily reduced to the corresponding quinolylmethanol of formula N, under standard conditions known to a person skilled in the art such as treatment in an alcoholic solvent (for example methanol) with sodium borohydride at a temperature comprised between 0° C. and 40° C.

The compounds of formula N in which $R_2$, $R_3$, $R_4$, $R_5$ and $R_6$ have the meaning indicated above, can also be obtained from carboxylated quinolones of formula

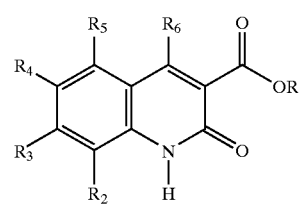

Q in which $R_2$, $R_3$, $R_4$, $R_5$ and $R_6$ have the meaning indicated above, according to the following process: a quinolone of formula Q is chlorinated to produce the corresponding chloroquinoline, the carboxylated function of which is reduced to produce the compound of general formula N. The chlorination can be carried out with a chlorophosphine oxide such as phosphorus oxychloride or chlorodiphenylphosphine oxide, pure or in the presence of an inert aprotic cosolvent such as toluene or chloroform, at a temperature comprised between 50° C. and 120° C. The chlorination is preferably carried out with an excess of phosphorus oxychloride at 80° C. The reduction can be carried out with an aluminium hydride in an aprotic solvent such as diethyl ether, tert-butylmethyl oxide, tetrahydrofuran, dichloromethane, chloroform, trichloroethane or toluene, at a temperature comprised between 0° C. and 50° C. The reduction is preferably carried out with diisobutylaluminium hydride in dichloromethane at ambient temperature.

The compounds of formula Q, in which and $R_6$ is a hydrogen atom and $R_2$, $R_3$, $R_4$ and $R_5$ have the meaning indicated above, can be obtained from anthranilic acids of formula

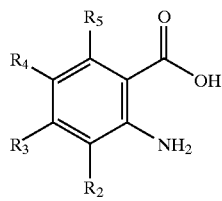

R in which $R_2$, $R_3$, $R_4$ and $R_5$ have the meaning indicated above, according to the following process: an acid of formula R is reduced to produce the corresponding benzyl alcohol. The alcohol function of the intermediate thus obtained is protected selectively in order to leave the amine function intact. The resulting aniline is acylated with a derivative of malonic acid. The previously protected alcohol function is deprotected, then oxidized to produce the corresponding carbonyl function, and the intermediate thus obtained is subjected to an intermolecular process according to a reaction known to a person skilled in the art under the name of Knovenagel's condensation, to produce carboxylated quinolones of formula Q, in which $R_6$ is a hydrogen atom and $R_2$, $R_3$, $R_4$ and $R_5$ have the meaning indicated above. The reduction of the acid to alcohol can be carried out by a metallic hydride in an inert aprotic solvent at a temperature comprised between 0° C. and 50° C., and preferably by a mixed hydride of lithium and aluminium in tetrahydrofuran at ambient temperature. The protection of the intermediate benzyl alcohol can be carried out according to the general methods known to the person skilled in the art (Greene T, et al., "Protective groups in Organic Synthesis", 2nd edition, Wiley, New-York, 1991) or also with a silyl chloride in the presence of a base, in an aprotic solvent at a temperature comprised between 0° C. and 50° C., and preferably by tert-butyldiphenylsilyl chloride in the presence of imidazole, in dimethylformamide at ambient temperature. Acylation can be carried out with a malonic derivative such as ethylmalonyl chloride or methyl malonate in the presence of a base such as triethylamine or 4-dimethylaminopyridine in an aprotic solvent such as acetonitrile, tetrahydrofuran or toluene at a temperature comprised between 0° C. and 110° C., and preferably with ethylmalonyl chloride in acetonitrile at ambient temperature in the presence of triethylamine. Deprotection can be carried out according to the protective group of the benzyl alcohol previously chosen (Greene, T.) and in the case of silylated ether by a fluoride ion source such as cesium or potassium fluoride in the presence of a phase transfer agent, or also tetrabutylammonium fluoride in an aprotic solvent such as tetrahydrofuran at a temperature comprised between 0° C. and 50° C. and preferably at ambient temperature. The oxidation can be carried out in the presence of chromium (VI) salts carrying pyridyl ligands, by Swern's reagent, or also by pyridine-sulphur trioxide complex in dimethyl sulphoxide in the presence of triethylamine, and preferably by pyridinium dichromate in dichloromethane at ambient temperature. Knoevenagel's intermolecular condensation can be carried out spontaneously or in solution in the presence of a base, and preferably in dichloromethane in the presence of triethylamine at ambient temperature.

The compounds of formula Q, in which $R_2$, $R_3$, $R_4$, $R_5$ and $R_6$ have the meaning indicated above, can be obtained from aminoketones of formula

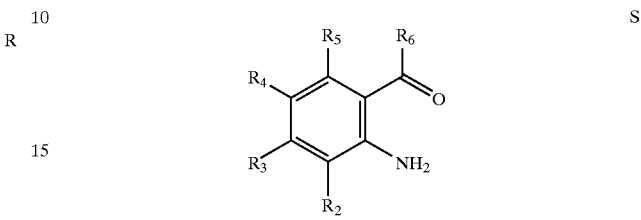

S in which $R_2$, $R_3$, $R_4$, $R_5$ and $R_6$ have the meaning indicated above, according to the following process: an aminoketone S is acylated with a derivative of malonic acid and the intermediate thus obtained is subjected to an intermolecular process according to a reaction known to a person skilled in the art under the name of Knovenagel's condensation to produce carboxylated quinolones of formula Q. Acylation can be carried out with a malonic derivative such as ethylmalonyl chloride or methyl malonate in the presence of a base such as triethylamine or 4-dimethylamino-pyridine in an aprotic solvent such as acetonitrile, tetrahydrofuran or toluene at a temperature comprised between 0° C. and 110° C., and preferably with ethylmalonyl chloride in acetonitrile at ambient temperature in the presence of triethylamine. Knovenagel's intermolecular condensation can be carried out spontaneously or in solution in the presence of a base, and preferably in acetonitrile in the presence of sodium ethylate at ambient temperature.

The aminoketones of formula S, in which $R_2$, $R_3$, $R_4$, $R_5$ and $R_6$ have the meaning indicated above, can be obtained from ortho-aminated benzonitriles of formula

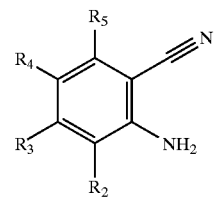

in which $R_2$, $R_3$, $R_4$ and $R_5$ have the meaning indicated above, by treatment with a Grignard's reagent of formula $R_6$—MgX, Where X is a halogen and $R_6$ has the meaning above according to methods known to the person skilled in the art.

The aminoketones of formula S, in which $R_6$ is an aryl radical and $R_2$, $R_3$, $R_4$ and $R_5$ have the meaning indicated above, can be obtained from anthranilic acids of formula R described above, by treatment with benzoyl chloride under reflux to produce a benzoxazone which can be converted in the presence of Grignard's reagent of formula $R_6$—MgX, where X is a halogen and $R_6$ is an aryl radical to the corresponding ortho-aminated benzophenone, which can be debenzoylated by reagents such as, for example, hydrogen bromide in solution in water or in glacial acetic acid.

The aminoketones of formula S, in which $R_2$, $R_3$, $R_4$, $R_5$ and $R_6$ have the meaning indicated above, can be obtained from anilines of formula P in which $R_2$, $R_3$, $R_4$ and $R_5$ have the meaning indicated above, according to the following process: the nitrogen atom of an aniline of formula P is acylated with an agent conferring an ortho-directive character in the aryl metallation reaction, and the compound thus obtained is metalated, then treated with an aldehyde of formula $R_6$—CHO in which $R_6$ has the meaning above. The process is then completed by oxidation of the alcoholic intermediate thus obtained, then by release of the nitrogenous function to produce an aminoketone of formula S. For this process, passage to the ortho-directive function can be obtained by treating an aniline P with a "bocant" agent and preferably by di-tert-butyl dicarbonate in an aprotic solvent such as tetrahydrofuran, dioxane or dimethoxyethane at reflux temperature. The metallation can be obtained by treatment with a lithiated reagent such as tert-butyllithium, sec-butyllithium, mesityllithium, or, in the presence of tetramethylethylenediamine, n-butyllithium, and preferably n-butyllithium in the presence of tetramethyl-ethylenediamine, in an aprotic solvent such as tetrahydrofuran, dioxane or dimethoxyethane, at a temperature comprised between −80° C. and 0° C. Oxidation can be carried out in the presence of chromium (VI) salts carrying pyridyl ligands, by Swern's reagent, or also by the pyridine-sulphur trioxide complex in dimethylsulphoxide in the presence of triethylamine, and preferably by pyridinium dichromate in dichloromethane under reflux. The nitrogenous function can be obtained by treatment in acid medium, and preferably by trifluoroacetic acid in dichloromethane at ambient temperature.

Analogues of intermediate compounds of type N have been described previously and in particular in the PCT Application WO 95/05427.

The compounds of formula (III)

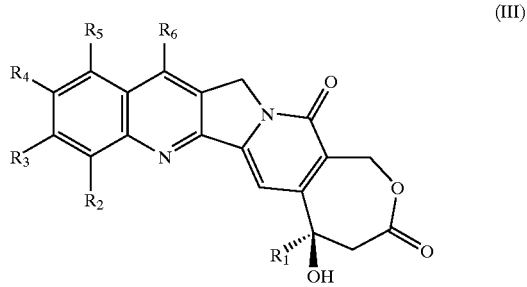

(III)

in which $R_1$ represents a lower alkyl radical;

$R_2$, $R_3$, $R_4$ and $R_5$ represent, independently, H, a halogen atom or —$OSO_2R_{10}$;

$R_6$ represents a linear or branched alkyl radical containing 1 to 12 carbon atoms optionnally substituted by one or more halo radicals indentical or different, lower hydroxy alkyl, lower alkoxy lower alkyl, lower cycloalkyl alkyl, —$(CH_2)_m\ SiR_7R_8R_9$ radical, or lower aryl alkyl radical substituted or non substituted on the aryl group, the substituents being identical or different and selected from: a lower alkyl, a hydroxy group, halo, amino, lower alkyl amino, di(lower alkyl)amino, $CF_3$ or $OCF_3$;

$R_7$, $R_8$ and $R_9$ represent, independently, a lower alkyl radical;

$R_{10}$ represents a lower alkyl radical optionnally substituted by one or more halo radicals identical or different, or an aryl optionnally susbtituted by one or more lower alkyl radicals identical or different;

m is an integer comprised between 0 and 6;

can also be obtained by a new process, characterized in that a compound of formula

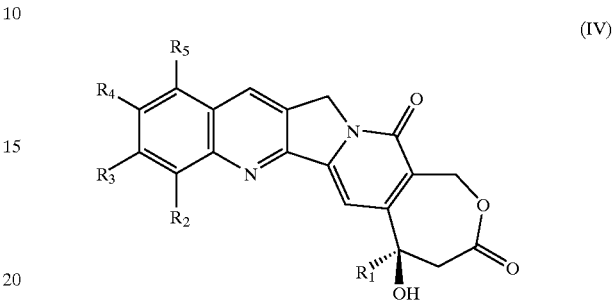

(IV)

in which $R_1$, $R_2$, $R_3$, $R_4$ and $R_5$ have the meaning indicated above, is treated in a strongly acid medium in the presence of an iron (III) salt and a precursor of the free radical $R_6$·, by a solution containing hydroxide or alkoxide radicals.

Although the prior art mentions the use of a similar reaction for the analogues of camptothecines containing an α-hydroxylactone (Sawada, S., et al., *Chem Pharm. Bull.*, (1991), vol. 39, p. 2574); PCT Application WO 98/35940), its use for the analogues of camptothecines such as the compounds of formula (IV) containing a β-hydroxylactone, has not been foreseen and is unexpected, because in strongly acid medium, a ternary and benzylic hydroxyl function, in position β with regard to a carboxylic function, is generally eliminated to produce the corresponding olefine (Nagasawa, et al. *Heterocycles* 1989, vol. 28, p. 703; Kimura, H. et al., *Chem. Pharm. Bull.* 1982, vol. 30, p. 552; Fujita, T. et al., *J. Appl Chem Biotechnol.* 1982, vol. 32, p. 421; Miller, R. E., et al., *J. Org. Chem.* 1950, vol. 15, p. 89; Fieser, L. F., et al., J. Am. Chem. Soc. 1948, vol. 70, p. 3209).

In the process above, the strongly acid medium can be provided by acids such as aqueous or non-aqueous trifluoroacetic acid or sulphuric acid and preferably aqueous sulphuric acid, the iron (III) salt will preferably be heptahydrated iron (III) sulphate, the free radical precursor will be an aldehyde of formula $R_6$—CHO in which $R_6$ represents an alkyl radical containing 1 to 12 carbon atoms optionnally substituted by one or more halo radicals identical or different, lower hydroxy alkyl, lower alkoxy lower alkyl, lower cycloalkyl alkyl, —$(CH_2)_m SiR_7R_8R_9$ radical, or lower aryl alkyl radical substituted or non substituted on the aryl group by one or more substituents being identical or different and selected from: lower alkyl, hydroxy, halo, amino, lower alkyl amino, di(lower alkyl)amino, $CF_3$ or $OCF_3$. The solution containing hydroxide or alkoxide radicals may be provided by hydrogen peroxide or tert-butyl hydroperoxide, and preferably by hydrogen peroxide at 30 volumes.

The compounds of the present invention possess useful pharmacological properties. Therefore it follows that the compounds of the present invention have an inhibitory activity of topoisomerase I and/or II and an anti-tumoral activity. The state of the art suggests that the compounds of the invention have an anti-parasitic and/or anti-viral activity. The compounds of the present invention can thus be used in different therapeutic applications.

An illustration of the pharmacological properties of the compounds of the invention will be found hereafter in the experimental part.

The compounds can inhibit topoisomerase, for example of type I and/or II, in a patient, for example a mammal such as man, by administration to this patient of a therapeutically effective quantity of the compounds of the invention.

The compounds of the invention have an anti-tumoral activity. They can be used for the treatment of tumors, for example of tumors expressing a topoisomerase, in a patient by administration to said patient of a therapeutically effective quantity of one of the compounds of the invention. Examples of tumors or cancers include cancers of the oesophagus, the stomach, the intestines, the rectum, the oral cavity, the pharynx, the larynx, the lung, the colon, the breast, the cervix uteri, the corpus endometrium, the ovaries, the prostate, the testicles, the bladder, the kidneys, the liver, the pancreas, the bone, the connective tissues, the skin, for example melanomas, the eyes, the brain and the central nervous system, as well as cancer of the thyroid, leukemia, Hodgkin's disease, lymphomas other than those related to Hodgkin, multiple myelomas and others.

They can also be used for the treatment of parasitic infections by inhibition of the hemoflagellates (for example in trypanosomia or leishmania infections) or by inhibition of the plasmodia (such as for example in malaria), but also the treatment of viral infections or diseases.

These properties make the compounds of the invention suitable for pharmaceutical use. A subject of the present application is also the compounds of the invention, and in particular the products of general formulae (I), (II$_A$) or (III) as defined above as medicaments. The invention also relates to pharmaceutical compositions containing at least one of the medicaments as defined above as an active ingredient.

Therefore the invention relates to pharmaceutical compositions containing a compound according to the invention or an addition salt with a pharmaceutically acceptable acid of it, in combination with a pharmaceutically acceptable support according to the chosen administration method (for example oral, intravenous, intraperitoneal, intramuscular, trans-dermic or sub-cutaneous). The pharmaceutical composition (for example therapeutic) can be in the form of a solid, liquid, liposome or lipidic micella.

The pharmaceutical composition can be in solid form, such as for example, powders, pills, granules, tablets, liposomes, gelatin capsules or suppositories. The pill, tablet or gelatin capsule can be covered in a substance which is capable of protecting the composition from the action of gastric acid or enzymes in the stomach of the subject for a sufficient period of time to allow this composition to pass in a non-digested form into the small intestine thereof. The compound can also be administered locally, for example, at the same location as the tumor. The compound can also be administered according to a sustained release process (for example a sustained release composition or an infusion pump). The appropriate solid supports can be, for example, calcium phosphate, magnesium stearate, magnesium carbonate, talc, sugars, lactose, dextrin, starch, gelatin, cellulose, methyl cellulose, sodium carboxymethyl cellulose, polyvinylpyrrolidine and wax. The pharmaceutical compositions containing a compound according to the invention can also be presented in liquid form such as, for example, solutions, emulsions, suspensions or a sustained release formulation. The appropriate liquid supports can be, for example, water, organic solvents such as glycerol or glycols such as polyethylene glycol, similarly their mixtures, in varied proportions, in water.

A subject of the invention is also the use of the compounds of the invention for the preparation of medicaments intended to inhibit topoisomerases, and more particularly the topoisomerases of type I or of type II, medicaments intended to treat tumors, medicaments intended to treat parasitic infections, as well as medicaments intended to treat viral infections or diseases.

The dose of a compound according to the present invention envisaged for the treatment of the diseases or disorders mentioned above, varies according to the administration method, the age and body weight of the subject as well as the state thereof and it will be method, the age and body weight of the subject as well as the state of the latter and it will be decided definitively by the attending doctor or vet. Such a quantity determined by the attending doctor or vet is here called "effective therapeutic quantity".

Unless defined in another manner, all the technical and scientific terms used here have the same meaning as that commonly understood by an ordinary specialist in the field to which the invention belongs. Similarly, all publications, patent applications, all patents and all other references mentioned here are incorporated by way of reference.

The following examples are presented to illustrate the above procedures and must in no case be considered as a limit to the scope of the invention.

EXPERIMENTAL PART

Example 1

(5R)-5-ethyl-11-fluoro-5-hydroxy-4,5,13,15-tetrahydro-1H,3H-oxepino[3',4':6,7]indolizino[1,2-b]quinoline-3,15-dione Stage 1a: quinidinium (3R)-3-(3-benzyloxymethyl-2-methoxy-4-pyridyl)-3-hydroxy-pentanoate Tert-butyl 3-(3-benzyloxymethyl-2-methoxy-4-pyridyl)-3-hydroxy-pentanoate (obtained according to the method described in the Patent Application WO 97/00876; 40 g; 100 mmol) is treated with trifluoroacetic acid (150 ml) and the reaction medium is agitated for 18 hours at 20° C., then concentrated under reduced pressure. The residue, taken up in a saturated aqueous solution of sodium bicarbonate (200 ml), is washed with dichloromethane (2×100 ml) and the resulting solution is acidified to pH=1 with 6 N hydrochloric acid, then extracted with dichloromethane (2×200 ml). The combined extracts are dried over magnesium sulphate and concentrated. The solution is dried over magnesium sulphate and concentrated. The racemic acid thus obtained (31.1 g; 90 mmol), taken up in isopropyl alcohol (30 ml), is treated with a quinidine solution (29.2 g; 90 mmol) in isopropyl alcohol (30 ml), and the resulting mixture is agitated at 50° C. until complete dissolution. The temperature is allowed to reduce to 40° C., the agitation is stopped and the reaction medium allowed to cool down to ambient temperature. The medium is taken to 0° C. without agitation then maintained at this temperature for 16 hours. Then the temperature is allowed to rise to 20° C. and agitation is carried out until crystallization. The medium is diluted with isopropyl alcohol then filtered. The precipitate is rinsed with isopropyl alcohol. The dextrorotatory salt precipitates whilst the levorotatory salt remains in solution in isopropyl alcohol. The filtrate is recovered which is concentrated to produce the expected product. Analysis by HPLC (column CHIRAL-AGP 5$\mu$ (10 cm×4 mm) eluted with an isopropyl alcohol/water/phosphate buffer mixture pH 6.5 30/920/50, at a flow rate of 1.2 ml/min, UV detection at 280 m) shows retention times of 6.4 min for the levorotatory salt and 2.8 min for the dextrorotatory salt and a diastereoisomeric ratio of 83/17.

Stage 1b: (5R)-5-ethyl-5-hydroxy-1,3,4,5,8,9-hexahydrooxepino[3,4-c]pyridin-3,9-dione, or (+)-EHHOPD The residue obtained in Stage 1a is agitated for 16 hours at 20° C. in a mixture of dichloromethane (270 ml) and 1N hydrochloric acid (270 ml). After decanting, the organic phase is concentrated, and the residue is taken up in methanol (87 ml) to be used in the following phase. This solution is poured under nitrogen onto Palladium at 10% on damp carbon at 50% (27.7 g; 13 mmol). The reaction medium is agitated for 5 min, then poured into a solution of ammonium formate (11.5 g; 183 mmol) in methanol (135 ml). The reaction medium is agitated for 30 min whilst allowing the temperature to rise, then it is heated at 40° C. for 30 min. The medium is then filtered on a bed of Clarcel and concentrated. Toluene (40 ml) is poured in followed by evaporation, and this operation is repeated in order to eliminate the traces of methanol. The residue, taken up in tetrahydrofuran (45 ml), is treated with a solution of dicyclohexylcarbodiimide (7.18 g; 34.5 mmol) in tetrahydrofuran (20 ml). The reaction medium is heated at 50° C. for 1 hour, then taken to 20° C., and the dicyclohexylurea is filtered. The filtrate is concentrated to dryness and the residue, taken up in acetonitrile (46 ml), is treated with sodium iodide (6.0 g; 40.5 mmol) and trimethylsilyl chloride (5.13 ml; 40.5 mmol). The reaction medium is maintained under agitation at ambient temperature for 5 hours, then acetonitrile (28 ml) and water (5.6 ml) are added. The precipitate obtained is recovered by filtration, then taken up in water (10 ml), and the mixture obtained is neutralized using a solution of ammonium hydroxide. The precipitate is recovered by filtration then taken up in acetone (40 ml) to which water (150 ml) is added. The crystals formed are recovered by filtration and dried to produce 3 g of (+)-EHHOPD with an enantiomeric proportion of 99.4/0.6.

NMR $^1$H (DMSO-d$_6$, δ): 0.8 (t, 3H); 1.65 (m, 2H); 3.00–3.35 (q, 2H); 5.3 (q, 2H); 5.7 (s, 1H); 6.35 (d, 1H); 7.3 (d, 1H); 11.7 (s, 1H).

Stage 1c: 2-amino-6-fluorophenylmethanol

A solution under argon of 2-amino-6-fluorobenzoic acid (5 g; 32 mmol) in anhydrous tetrahydrofuran (100 ml) is treated with lithium aluminium hydride (1M in tetrahydrofuran; 64 ml 64 mmol) at ambient temperature. The reaction medium is agitated for 3 hours, then hydrolyzed at 0° C. with a saturated aqueous solution of ammonium chloride (100 ml). The resulting mixture is extracted with ethyl acetate (2×70 ml). The combined extracts are washed with water and with a saturated aqueous solution of sodium chloride, then dried over magnesium sulphate and concentrated to produce 3.8 g of the desired product, a white solid (m.p.: 93° C.).

IR(KBr): 784, 1001, 1471, 1591, 1621 cm$^{-1}$.

NMR $^1$H (DMSO-d$_6$, δ): 4.44 (dd, 2H); 4.93 (t, 1H); 5.27 (s, 2H); 6.27 (t, 1H); 6.45 (d, 1H); 6.96 (q, 1H).

Stage 1d: ethyl 2-(3-fluoro-2-hydroxymethylphenylcarbamoyl)acetate

A solution of aminobenzyl alcohol (obtained in Stage 1c; 3.8 g; 27 mmol) and imidazole (4.3 g; 64 mmol) in N,N-dimethylformamide (52 ml) is treated with tert-butyldiphenylsilyl chloride (8.37 ml; 32 mmol). The resulting mixture is agitated for 2 hours at ambient temperature, then water (100 ml) is added, followed by extraction with ethyl acetate (2×60 ml). The combined extracts are washed with water and with a saturated aqueous solution of sodium chloride, then dried over magnesium sulphate and concentrated. The silylated intermediate thus obtained (10 g) is taken up in acetonitrile (52 ml), then triethylamine (4.5 ml; 32.4 mmol) is added to the solution, and the resulting mixture is treated dropwise with ethylmalonyl chloride (4.15 ml; 32.4 mmol). The resulting mixture is agitated for 2 hours at ambient temperature, then water (100 ml) is added, followed by extraction with ethyl acetate (2×60 ml). The combined extracts are washed with water and with a saturated aqueous solution of sodium chloride, then dried over magnesium sulphate and concentrated. The residue (16 g) is taken up in tetrahydrofuran (50 ml) and treated dropwise with tetrabutylammonium fluoride (1M in tetrahydrofuran; 27 ml; 27 mmol). The resulting mixture is agitated for 1 hour at ambient temperature, then water (100 ml) is added followed by extraction with ethyl acetate (2×60 ml). The combined extracts are washed with water and with a saturated solution of sodium chloride, then dried over magnesium sulphate and concentrated. Purification of the residue by chromatography at medium pressure (SiO$_2$, CH$_2$Cl$_2$/MeOH, 95/5) yields 4.8 g of a white solid (m.p.: 91° C.).

IR (KBr): 1472, 1542, 1589, 1657, 1719, 3286, 3482 cm$^{-1}$.

NMR $^1$H (DMSO-d$_6$, δ) 1.19 (t, 3H); 3.54 (s, 2H); 4.14 (q, 2H); 4.55 (dd, 2H); 5.21 (t, 1H); 6.97 (t, 1H); 7.31 (dd, 1H); 7.53 (d, 1H).

Stage 1e: ethyl 5-fluoro-2-oxo-1,2-dihydro-3-quinolinecarboxylate

A solution of malonic derivative (obtained in Stage 1d; 4.8 g; 19 mmol) in dichloromethane (280 ml) is treated with pyridinium dichromate (8.3 g; 22 mmol). The resulting suspension is agitated for 4 hours at ambient temperature, then treated with triethylamine (30 ml; 220 mmol). The reaction medium is agitated at ambient temperature for 16 hours, then concentrated under reduced pressure. Purification of the residue by chromatography at medium pressure (SiO$_2$, CH$_2$Cl$_2$/MeOH, 95/5) yields 2.1 g of a yellow solid (m.p.: 180° C.).

IR(KBr): 1441, 1498, 1655, 1747 cm$^{-1}$.

NMR $^1$H (DMSO-d$_6$, δ) 1.31 (t, 3H); 4.28 (q, 2H); 7.06 (t, 1H); 7.16 (d, 1H) 7.61 (dd, 1H); 8.43 (s, 1H); 12.27 (s, 1H).

Stage 1f: ethyl 2-chloro-5-fluoro-3-quinolinecarboxylate

The quinolone (obtained in Stage 1e; 2.1 g) is heated at 80° C. in phosphorus oxychloride (14 ml) until the reaction is complete (TLC control: SiO$_2$, CH$_2$Cl$_2$/MeOH, 95/5). The resulting solution is then concentrated under reduced pressure and the residue is taken up in water. The precipitate thus formed is recovered by filtration, washed with water until the pH is neutral, and dried under reduced pressure in the presence of phosphorus pentoxide to produce 1.8 g of a white solid (m.p.: 97° C.).

IR(KBr) 1268, 1631, 1723 cm$^{-1}$.

NMR $^1$H (DMSO-d$_6$, δ): 1.38 (t, 3H); 4.42 (q, 2H); 7.60 (t, 1H); 7.89 (d, 1H); 7.97 (dd, 1H); 8.92 (s, 1H).

Stage 1g: 2-chloro-5-fluoro-3-quinolylmethanol

A solution of quinolinecarboxylate (obtained in Stage 1f; 1.8 g; 6.7 mmol) in dichloromethane (40 ml) under argon is treated dropwise with diisobutylaluminium hydride (1M in dichloromethane; 20 ml; 20 mmol) at ambient temperature maintained at 10° C. by an ice-cooled water bath. The reaction mixture is agitated for 1 hour at ambient temperature, then poured onto a solution of sodium and potassium tartrate at 20% (200 ml). The resulting mixture is agitated vigorously for 1 hour, then filtered on celite. The filtrate is extracted with dichloromethane (2×100 ml). The combined extracts are washed with water and with a saturated solution of sodium chloride, then dried over magnesium sulphate and concentrated. Purification of the residue by chromatography at medium pressure (SiO$_2$, CH$_2$Cl$_2$/MeOH, 98/2) yields 450 mg of a white solid (m.p. 176° C.).

NMR $^1$H (DMSO-d$_6$, δ): 4.71 (d, 2H); 5.78 (t, 3H); 7.51 (t, 1H); 7.75–7.83 (m, 2H); 8.50 (s, 1H).

Stage 1h: (5R)-5-ethyl-11-fluoro-5-hydroxy-4,5,13,15-tetrahydro-1H,3H-oxepino[3',4':6,7]indolizino[1,2-b]quinoline-3,15-dione A solution of quinolylmethanol (obtained in Stage 1g; 422 mg; 2 mmol), of (+)-EHHOPD (obtained in Stage 1b; 446 mg; 2 mmol) and triphenylphosphine (592 mg; 2.2 mmol) in N,N-dimethylformamide (8 ml) is treated dropwise with isopropyl azodicarboxylate (0.43 ml; 2.2 mmol). The reaction mixture is agitated for 16 h at ambient temperature, then water (100 ml) is added, followed by extraction with ethyl acetate (2×100 ml). The combined extracts are washed with water and with a saturated solution of sodium chloride, then dried over magnesium sulphate and concentrated under reduced pressure. The residue is purified by chromatography at medium pressure (SiO$_2$, AcOEt/heptane, 30/70). A mixture under argon of the intermediate obtained (325 mg; 0.78 mmol), triphenylphosphine (42 mg; 0.156 mmol), potassium acetate (114 mg; 1.17 mmol), tetrabutylammonium bromide (276 mg; 0.86 mmol) and palladium acetate (0.078 mmol) is taken to reflux in anhydrous acetonitrile for 16 hours, then cooled down to ambient temperature and concentrated under reduced pressure. The residue is purified by chromatography at medium pressure (SiO$_2$, MeOH/CH$_2$Cl$_2$, 5/95) to produce 80 mg of the expected solid (m.p.>250° C.).

IR (KBr): 1659, 1734, 3386 cm$^{-1}$.

NMR $^1$H (DMSO-d$_6$, δ): 0.86 (t, 3H); 1.85 (q, 2H); 3.07 (d, 1H); 3.46 (d, 1H); 5.28 (s, 2H); 5.39 (d, 1H); 5.52 (d, 1H); 6.02 (s, 1H); 7.43 (s, 1H); 7.55 (t, 1H); 7.85 (q, 1H); 8.01 (d, 1H); 8.82 (s, 1H).

Example 2

(5R)-5-ethyl-9-fluoro-5-hydroxy-4,5,13,15-tetrahydro-1H,3H-oxepino[3',4':6,7]indolizino[1,2-b]quinoline-3,15-dione This compound is obtained by applying Stages 1c to 1h of the operating method of Example 1 above to 2-amino-4-fluorobenzoic acid. A solid (m.p.>250° C.) is obtained.

NMR $^1$H (DMSO-d$_6$, δ): 0.86 (t, 3H); 1.84 (q, 2H); 3.04 (d, 1H); 3.47 (d, 1H); 5.24 (s, 2H); 5.39 (d, 1H); 5.52 (d, 1H); 6.06 (s, 1H); 7.39 (s, 1H); 7.65 (t, 1H); 7.88 (d, 1H); 8.22 (dd, 1H); 8.71 (s, 1H).

Example 3

(5R)-5-ethyl-8-fluoro-5-hydroxy-4,5,13,15-tetrahydro-1H,3H-oxepino[3',4':6,7]indolizino[1,2-b]quinoline-3,15-dione This compound is obtained by applying Stages 1c to 1h of the operating method of Example 1 above to 2-amino-3-fluorobenzoic acid (prepared according to Muchowski, et al., *J. Org Chem.*, vol. 45, p. 4798). A solid (m.p.>250° C.) is obtained.

IR (KBr): 1659, 1731, 3344 cm$^{-1}$.

NMR $^1$H (DMSO-d$_6$, δ): 0.88 (t, 3H); 1.85 (q, 2H); 3.07 (d, 1H); 3.47 (d, 1H); 5.29 (s, 2H); 5.40 (d, 1H); 5.53 (d, 1H); 6.06 (s, 1H); 7.44 (s, 1H); 7.69 (m, 2H); 7.96 (m, 1H); 8.75 (s, 1H).

Example 4

(5R)-12-benzyl-5-ethyl-5-hydroxy-4,5,13,15-tetrahydro-1H,3H-oxepino[3',4':6,7]indolizino[1,2-b]quinoline-3,15-dione

Stage 4a: 1-(2-aminophenyl)-2-phenyl-1-ethanone

A solution of 2-aminobenzonitrile (4.25 g, 36 mmol) in anhydrous diethyl ether (40 ml) at 0° C. is treated under argon with benzylmagnesium chloride (2M in tetrahydrofuran; 50 ml; 100 mmol). The reaction medium is maintained under agitation for 1 hour at ambient temperature, then hydrolyzed at 0° C. by adding hydrochloric acid at 10%, agitated for 1 hour, and neutralized with sodium hydroxide. The resulting mixture is extracted with ethyl acetate. The combined extracts are washed with water and with a saturated solution of sodium chloride, then dried over magnesium sulphate and concentrated to produce 3.5 g of the desired product, in the form of a white solid (m.p.: 100–101° C.).

IR (KBr): 1469, 1612, 1725 cm$^{-1}$

NMR $^1$H (DMSO-d$_6$, δ): 4.25 (s, 2H); 6.53 (t, 1H); 6.74 (d, 1H); 7,2-7.35 (m, 8H); 7.90 (d, 1H).

Stage 4b: ethyl 4-benzyl-2-oxo-1,2-dihydro-3-quinolinecarboxylate

A solution of amino-ketone (obtained in Stage 4a; 13.5 g; 16 mmol) and triethylamine (3.9 ml, 28 mmol) in acetonitrile (66 ml) is treated at 10° C. dropwise with ethylmalonyl chloride (3.64 ml; 28 mmol). The reaction medium is agitated for 16 hours at ambient temperature, then treated with sodium ethoxide, obtained by dissolution of sodium (0.4 g; 17 mmol) in ethanol (25 ml). The resulting mixture is agitated for 16 hours at ambient temperature, then water is added (200 ml), followed by extraction with dichloromethane (2×100 ml). The combined extracts are washed with water and with a saturated solution of sodium chloride, then dried over magnesium sulphate and concentrated. The residue is taken up in ethyl ether to produce a precipitate which is recovered by filtration, dried under reduced pressure at 50° C., to produce the expected solid (m.p.: 230° C.).

NMR $^1$H (DMSO-d$_6$, δ): 1.19 (t, 3H); 4.17 (s, 2H); 4.27 (q, 2H); 7.13 (t, 1H); 7.15–7.20 (m, 1H); 7.20–7.40 (m, 5H); 7.49 (t, 1H); 7.69 (d, 1H); 12.15 (s, 1H).

Stage 4c: (5R)-12-benzyl-5-ethyl-5-hydroxy-4,5,13,15-tetrahydro-1H,3H-oxepino[3',4':6,7]indolizino[1,2-b]quinoline-3,15-dione Stages 1f to 1h of the operating method of Example 1 above are applied to the quinolone obtained according to Stage 4b. A solid is obtained (m.p.>250° C.).

IR(KBr): 1578, 1655, 1751 cm$^{-1}$.

NMR $^1$H (DMSO-d$_6$, δ): 0.87 (t, 3H); 1.87 (q, 2H); 3.05 (d, 1H); 3.49 (d, 1H); 4.65 (d, 1H); 4.70 (d, 1H); 5.20 (d, 1H); 5.25 (d, 1H); 5.39 (d, 1H); 5.52 (d, 1H); 6.06 (s, 1H); 7.15-7.30 (m, 5H); 7.41 (s, 1H); 7.67 (t, 1H); 7.83 (t, 1H); 8.16 (d, 1H); 8.28 (d, 1H).

Example 5

(5R)-12-butyl-5-ethyl-5-hydroxy-4,5,13,15-tetrahydro-1H,3H-oxepino[3',4':6,7]indolizino[1,2-b]quinoline-3,15-dione 2-aminobenzonitrile is treated with n-butylmagnesium bromide according to a procedure similar to Stage 4a and the resulting amino-ketone is treated according to a procedure similar to Stage 4b. Stages 1f to 1h of the operating method of Example 1 above are applied to the quinolone obtained. A solid is obtained (m.p. 220–221° C.).

IR (KBr): 1611; 1655; 1725 cm$^{-1}$.

NMR $^1$H (DMSO-d$_6$, δ): 0.87 (t, 3H); 0.96 (t, 3H); 1.49 (q, 2H); 1.67 (q, 2H); 1.86 (q, 2H); 3.05 (d, 1H); 3.19 (t, 2H); 3.49 (d, 1H); 5.28 (s, 2H); 5.40 (d, 1H); 5.54 (d, 1H); 6.05 (s, 1H); 7.39 (s, 1H); 7.72 (t, 1H); 7.85 (t, 1H); 8.14 (d, 1H); 8.26 (d, 1H).

Example 6

(5R)-5,12-diethyl-5-hydroxy-4,5,13,15-tetrahydro-1H,3H-oxepino[3',4':6,7]indolizino[1,2-b]quinoline-3,15-dione 2-aminobenzonitrile is treated with ethylmagnesium bromide according to a procedure similar to Stage 4a and the resulting amino-ketone is treated according to a procedure similar to Stage 4b. Stages 1f to 1h of the operating method of Example 1 above are applied to the quinolone obtained. A solid is obtained (m.p.>280° C.).

IR (KBr): 1652, 1758, 3329 cm$^{-1}$.

NMR $^1$H (DMSO-d$_6$, δ): 0.85 (t, 3H); 1.31 (t, 3H); 1.87 (q, 2H); 3.04 (d, 1H); 3.24 (q, 2H); 3.54 (d, 1H); 5.25 (s, 2H); 5.36 (d, 1H); 5.53 (d, 1H); 6.06 (s, 1H); 7.39 (s, 1H); 7.72 (t, 1H); 7.85 (t, 1H); 8.15 (d, 1H); 8.28 (d, 1H).

Example 7

(5R)-5-ethyl-5-hydroxy-12-phenyl-4,5,13,15-tetrahydro-1H,3H-oxepino[3',4':6,7]indolizino[1,2-b]quinoline-3,15-dione 2-aminophenyl-phenylmethanone is treated according to a procedure similar to Stage 4b. Stages 1f to 1h of the operating method of Example 1 are applied to the quinolone obtained. A solid is obtained (m.p.>250° C.).

NMR $^1$H (DMSO-d$_6$, δ): 0.86 (t, 3H); 1.85 (q, 2H); 3.05 (d, 1H); 3.49 (d, 1H); 5.09 (s, 2H); 5.38 (d, 1H); 5.50 (d, 1H); 6.07 (s, 1H); 7.45 (s, 1H); 7.60–7.75 (m, 6H); 7.82 (d, 1H); 7.90 (t, 1H); 8.25 (d, 1H).

Example 8

(5R)-12-cyclohexyl-5-ethyl-5-hydroxy-4,5,13,15-tetrahydro-1H,3H-oxepino[3',4':6,7]indolizino[1,2-b]quinoline-3,15-dione 2-aminobenzonitrile is treated with cyclohexylmagnesium chloride according to a procedure similar to Stage 4a and the resulting amino-ketone is treated according to a procedure similar to that of Stage 4b. Stages 1f to 1h of the operating method of Example 1 above are applied to the quinolone obtained. A solid is obtained (m.p.>250° C.).

IR (KBr): 1655, 1728, 3500 cm$^{-1}$.

NMR $^1$H (DMSO-d$_6$, δ): 0.86 (t, 3H); 1.42 (t, 1H); 1.59 (t, 2H); 1.84 (m, 9H); 3.04 (d, 1H); 3.48 (d, 1H); 3.69 (m, 1H); 5.39 (d, 1H); 5.40 (s, 2H); 5.53 (d, 1H); 6.06 (s, 1H); 7.38 (s, 1H); 7.70 (t, 1H); 7.83 (t, 1H); 8.13 (d, 1H); 8.37 (s, 1H).

Example 9

(5R)-5-ethyl-5-hydroxy-12-(4-methylphenyl)-4,5,13,15-tetrahydro-1H,3H-oxepino[3',4':6,7]indolizino[1,2-b]quinoline-3,15-dione 2-aminophenyl-4-methylphenylmethanone is treated according to a procedure similar to Stage 4b. Stages 1f to 1h of the operating method of Example 1 above are applied to the quinolone obtained. A solid is obtained (m.p.>280° C.).

IR (KBr): 1655, 1754, 3407 cm$^{-1}$.

NMR $^1$H (DMSO-d$_6$, δ): 0.87 (t, 3H); 1.87 (q, 2H); 2.47 (s, 3H); 3.07 (d, 1H); 3.48 (d, 1H); 5.07 (d, 2H); 5.39 (d, 1H); 5.49 (d, 1H); 6.04 (s, 1H); 7.45 (s, 1H); 7.48 (m, 2H); 7.54 (m, 2H); 7.65 (m, 1H); 7.85 (m, 2H); 8.22 (d, 1H).

Example 10

(5R)-10-chloro-5-ethyl-12-(2-fluorophenyl)-5-hydroxy-4,5,13,15-tetrahydro-1H,3H-oxepino[3',4':6,7]indolizino[1,2-b]quinoline-3,15-dione 2-amino-5-chlorophenyl-2-fluorophenylmethanone is treated according to a procedure similar to that of Stage 4b. Stages 1f to 1h of the operating method of Example 1 above are applied to the quinolone obtained. A solid is obtained (m.p.>250° C.).

IR(KBr): 1656, 1744, 3397 cm$^{-1}$.

NMR $^1$H (DMSO-d$_6$, δ): 0.86 (t, 3H); 1.85 (q, 2H); 3.06 (d, 1H); 3.47 (d, 1H); 4.93 (d, 1H); 5.17 (d, 1H); 5.37 (d, 1H); 5.49 (d, 1H); 6.05 (s, 1H); 7.46 (s, 1H); 7.50–7.65 (m, 3H); 7.65–7.80 (m, 2H); 7.91 (d, 1H); 8.27 (d, 1H).

Example 11

(5R)-5-ethyl-9,10-difluoro-5-hydroxy-12-phenyl-4,5,13,15-tetrahydro-1H,3H-oxepino[3',4':6,7]indolizino [1,2-b]quinoline-3,15-dione Stage 11a: 6,7-difluoro-2-phenyl-4H-benzo[d][3.1]oxazine-4-one A mixture of 2-amino-4,5-difluorobenzoic acid (3.46 g; 20 mmol) and benzoyl chloride (56 ml; 480 mmol) is taken to reflux for 16 hours, then poured into a saturated aqueous solution of sodium bicarbonate (200 ml) and agitated at 80° C. for 2 hours. The resulting mixture is extracted with dichloromethane (2×100 ml). The combined extracts are washed with water and with a saturated solution of sodium chloride, then dried over magnesium sulphate and concentrated under reduced pressure. The residue is taken up in ethyl ether and the precipitate thus formed is recovered by filtration, washed with ethyl ether, and dried under reduced pressure to produce 3.2 g of a white solid (m.p.: 154° C.).

IR (KBr): 1613, 1657, 3341, 3467 cm$^{-1}$.

NMR $^1$H (DMSO-d$_6$, δ): 7.5–7.8 (m, 3H); 7.8–7.9 (m, 1H); 8.1–8.3 (m, 1H).

Stage 11b:
2-benzoyl-4,5-difluoro-1-phenylcarboxamidobenzene

A suspension of benzoxazine (obtained according to Stage 11a; 6.78 g; 26 mmol) in dichloromethane (260 ml) is treated dropwise under argon at −78° C. with phenylmagnesium bromide (3M in ethyl ether; 22 ml; 66 mmol). The resulting mixture is agitated at −78° C. for 1 hour, then hydrolyzed by adding a saturated aqueous solution of ammonium chloride (200 ml) and extracted with dichloromethane (2×100 ml). The combined extracts are washed with water and with a saturated solution of sodium chloride, then dried over magnesium sulphate and concentrated under reduced pressure. The residue taken up in isopropyl ether produces whites crystals which are recovered by filtration and dried. 7.3 g of product is obtained (m.p.: 58–59° C.).

IR (KBr): 1423, 1537, 1599, 1682 cm$^{-1}$.

NMR $^1$H (DMSO-d$_6$, δ): 7.4–7.6 (m, 9H); 7.69 (d, 2H); 7.88 (dd, 1H).

Stage 11 c:
2-amino-4,5-difluorophenyl-phenylmethanone

A solution of N-benzoylated amino-ketone (obtained according to Stage 11b; 7.3 g 21.7 mmol) in glacial acetic acid (300 ml) is treated with hydrobromic acid at 48% (150 ml) and the reaction medium is taken to reflux for 10 hours. After cooling down to ambient temperature, the resulting mixture is concentrated under reduced pressure, then taken up in a saturated aqueous solution of sodium bicarbonate (200 ml) and extracted with ethyl acetate (2×100 ml). The combined extracts are washed with water and with a saturated solution of sodium chloride, then dried over magnesium sulphate and concentrated under reduced pressure. The residue is taken up with pentane and the precipitate thus formed is recovered by filtration to produces 4 g of a light yellow solid (m.p.: 100–101° C.).

IR(KBr): 1514, 1563, 1645, 3372, 3482 cm$^{-1}$.

NMR $^1$H (DMSO-d$_6$, δ): 6.83 (dd, 1H); 7.1–7.4 (m, 3H); 7.5–7.7 (m, 5H).

Stage 11d: (5R)-5-ethyl-9,10-difluoro-5-hydroxy-12-phenyl-4,5,13,15-tetrahydro-1H,3H-oxepino[3',4':6,7]indolizino[1,2-b]quinoline-3,15-dione The aminoketone obtained in Stage 11c is treated according to a procedure similar to that of Stage 4b. Stages 1f to 1h of the operating method of Example 1 above are applied to the quinolone obtained. A solid is obtained (m.p.>250° C.).

IR (KBr): 1659, 1734, 3386 cm$^{-1}$.

NMR $^1$H (DMSO-d$_6$, δ): 0.85 (t, 3H); 1.80 (q, 2H); 3.06 (d, 1H); 3.45 (d, 1H); 5.00 (d, 1H); 5.35 (d, 1H); 5.48 (d, 1H); 6.03 (s, 1H); 7.39 (s, 1H); 7.55–7.75 (m, 6H); 8.24 (dd, 1H).

Example 12

(5R)-5-ethyl-9-fluoro-5-hydroxy-12-phenyl-4,5,13,15-tetrahydro-1H,3H-oxepino[3',4':6,7]indolizino[1,2-b]quinoline-3,15-dione 2-amino-4-fluorobenzoic acid is treated according to a procedure similar to Stages 11 a to 11c and the resulting aminoketone is treated according to a procedure similar to Stage 4b. Stages 1f to 1h of the operating method of Example 1 above are applied to the quinolone obtained. A solid is obtained (m.p.>250° C.).

NMR $^1$H (DMSO-d$_6$, δ): 0.86 (t, 3H); 1.84 (q, 2H); 3.06 (d, 1H); 3.46 (d, 1H); 5.00 (d, 1H); 5.08 (d, 1H); 5.37 (d, 1H); 5.49 (d, 1H); 6.03 (s, 1H); 7.43 (s, 1H); 7.50–7.80 (m, 6H); 7.85 (t, 1H); 7.96 (d, 1H).

Example 13

(5R)-12-butyl-5-ethyl-9,10-difluoro-5-hydroxy-4,5,13,15-tetrahydro-1H,3H-oxepino[3',4':6,7]indolizino[1,2-b]quinoline-3,15-dione Stage 13a: N-(3,4-difluorophenyl)acetamide A mixture of 3,4-difluoroaniline (50 ml; 500 mmol) and triethylamine (70 ml; 500 mmol) in dichloromethane (1.5 l) is cooled down using an ice bath. Acetic anhydride (71.5 ml; 750 mmol) is added dropwise and the reaction mixture is agitated for 1 hour at ambient temperature. The mixture obtained is then washed sequentially with water, with a solution of sodium bicarbonate at 10%, and with a saturated solution of sodium chloride. The organic fraction, dried over sodium sulphate, is concentrated under reduced pressure. The residue is suspended in pentane, filtered and dried under reduced pressure in order to produce the expected anilide, a beige solid (m.p.: 126–127.5° C.).

NMR $^1$H (DMSO-d$_6$, δ): 2.15 (s, 3H); 7.10–7.65 (m, 2H); 7.65–8.10 (m, 1H) 10.30 (broad peak, 1H).

Stage 13b:
2-chloro-6,7-difluoro-3-quinolinecarbaldehyde

The acetanilide obtained according to Stage 13a (32 g; 220 mmol) is added to a Vilsmeyer's reagent obtained under argon with anhydrous N,N-dimethylformamide (34 ml; 440 mmol) cooled down using an ice bath, treated dropwise with phosphorus oxychloride (103 ml; 1.1 mol), then agitated for 0.5 hours before allowing the temperature to rise to ambient temperature. The mixture thus obtained is agitated at 70° C. for 16 hours, then cooled down to ambient temperature. The reaction medium is then poured dropwise into a water-ice mixture (400 ml), and the resulting mixture is agitated for 2 hours. The precipitate obtained is filtered and washed with water until the pH is neutral, then dried under reduced pressure in the presence of phosphorus pentoxide in order to produce a yellow solid (m.p.: 226–229° C.).

IR(KBr): 888, 1061, 1262, 1507, 1691 cm$^{-1}$.

NMR $^1$H (DMSO-d$_6$, δ): 8.17 (dd, 1H); 8.39 (dd, 1H); 8.97 (d, 1H); 10.34 (d, 1H).

Stage 13c: 2-chloro-6,7-difluoro-3-quinolylmethanol

A suspension of quinoline-carbaldehyde obtained according to Stage 13b (9 g; 39 mmol) in methanol (400 ml) is treated with sodium borohydride (2 g; 53 mmol) at ambient temperature for 0.5 h. The excess borohydride is destroyed by acetic acid (2 ml) and the reaction medium is concentrated under reduced pressure. The residue, taken up in ethyl acetate (500 ml), is washed sequentially with an aqueous solution of sodium bicarbonate at 10%, with water, and with a saturated aqueous solution of sodium chloride. The organic phase, dried over magnesium sulphate, is concentrated under reduced pressure. The residue is recrystallized from 1,2-dichloroethane in order to produce the expected quinolylmethanol, a beige solid (m.p.: 166.5–167° C.).

IR(KBr): 871, 1038, 1253, 1513 cm$^{-1}$.

NMR $^1$H (DMSO-d$_6$, δ): 4.67 (d, 2H); 5.80 (t, 1H); 8.01 (dd, 1H); 8.22 (dd, 1H); 8.48 (s, 1H).

Stage 13d: (5R)-5-ethyl-9,10-difluoro-5-hydroxy-4,5,13,15-tetrahydro-1H,3H-oxepino[3',4':6,7]indolizino[1,2-b]quinoline-3,15-dione The quinolylmethanol obtained in Stage 13c is treated with (+)-EHHOPD according to the procedure in Stage 1h. A white solid is obtained.

IR (KBr): 871, 1261, 1512, 1579, 1654, 1746 cm$^{-1}$.

NMR $^1$H (DMSO-d$_6$, δ): 0.87 (t, 3H); 1.85 (m, 2H); 3.08 (d, 1H); 3.44 (d, 1H); 5.26 (s, 2H); 5.39 (d, 2H); 5.52 (d, 1H); 5.99 (s, 1H); 7.39 (s, 1H); 8.15 (dd, 1H); 8.23 (dd, 1H); 8.68 (s, 1H).

Stage 13e: (5R)-12-butyl-5-ethyl-9,10-difluoro-5-hydroxy-4,5,13,15-tetrahydro-1H,3H-oxepino[3',4':6,7]indolizino[1,2-b]quinoline-3,15-dione The product of Stage 13d (100 mg; 0.25 mmol) is dissolved in a mixture of water (1.33 ml) and sulphuric acid at 95% (1 ml). Heptahydrated iron (II) sulphate (28 mg 0.10 mmol) and valeraldehyde (0.17 ml; 1.60 mmol) are added to this solution and the resulting solution is cooled down with an ice bath. The reaction medium is then treated dropwise with hydrogen peroxide at 30% (0.38 ml; 1 mmol), agitated for 5 hours at ambient temperature, then diluted with water (50 ml) and extracted with dichloromethane (4×50 ml). The combined extracts are washed with water and with a saturated aqueous solution of sodium chloride, then dried over magnesium sulphate and concentrated under reduced pressure. The residue is purified by chromatography at medium pressure (SiO$_2$, MeOH/CH$_2$Cl$_2$, 5/95) in order to produce the expected solid (m.p.>275° C.).

IR (KBr): 1656, 1748, 3385 cm$^{-1}$.

NMR $^1$H (DMSO-d$_6$, δ): 0.85 (t, 3H); 0.94 (t, 3H); 1.47 (q, 2H); 1.64 (m, 2H); 1.83 (q, 2H); 3.05 (d, 1H); 3.16 (m, 2H); 3.47 (d, 1H); 5.27 (s, 2H); 5.39 (d, 1H); 5.52 (d, 1H); 6.05 (s, 1H); 7.35 (s, 1H); 8.13 (m, 1H); 8.32 (m, 1H).

Example 14

(5R)-12-benzyl-5-ethyl-9,10-difluoro-5-hydroxy-4,5,13,15-tetrahydro-1H,3H-oxepino[3',4':6,7]indolizino[1,2-b]quinoline-3,15-dione The product of Stage 13d is treated with phenylacetaldehyde according to a procedure similar to that of Stage 13e in order to produce the expected solid (m.p. 275° C. (dec.)).

IR (KBr): 1656, 1707, 1749 cm$^{-1}$.

NMR $^1$H (DMSO-d$_6$, δ): 0.86 (t, 3H); 1.84 (q, 2H); 3.05 (d, 1H); 3.48 (d, 1H); 4.64 (s, 2H); 5.19 (d, 2H); 5.38 (d, 1H); 5.51 (d, 1H); 6.06 (s, 1H); 7.20 (m, 1H); 7.26 (m, 4H); 7.37 (s, 1H); 8.15 (t, 1H); 8.31 (t, 1H).

Example 15

(5R)-5-ethyl-9,10-difluoro-5-hydroxy-12-propyl-4,5,13,15-tetrahydro-1H,3H-oxepino[3',4':6,7]indolizino[1,2-b]quinoline-3,15-dione The product of Stage 13d is treated with butyraldehyde according to a procedure similar to that of Stage 13e in order to produce the expected solid (m.p. 250° C.).

IR (KBr): 1656, 3425 cm$^{-1}$.

NMR $^1$H (DMSO-d$_6$, δ): 0.86 (t, 3H); 1.04 (t, 3H); 1.70 (q, 2H); 1.84 (q, 2H); 3.07 (d, 1H); 3.15 (t, 2H); 3.46 (d, 1H); 5.25 (s, 1H); 5.39 (d, 1H); 5.52 (d, 1H); 6.02 (s, 1H); 7.36 (s, 1H); 8.12 (m, 1H); 8.34 (m, 1H).

Example 16

(5R)-5,12-diethyl-9,10-difluoro-5-hydroxy-4,5,13,15-tetrahydro-1H,3H-oxepino[3',4':6,7]indolizino[1,2-b]quinoline-3,15-dione The product of Stage 13d is treated with propionaldehyde according to a procedure similar to that in Stage 13e in order to produce the expected solid (m.p.>275° C.).

IR (KBr): 1656, 1725, 3308 cm$^{-1}$.

NMR $^1$H (DMSO-d$_6$, δ): 0.85 (t, 3H); 1.28 (t, 3H); 1.83 (q, 2H); 3.05 (d, 1H); 3.19 (q, 2H); 3.47 (d, 1H); 5.29 (s, 2H); 5.39 (d, 1H); 5.52 (d, 1H); 6.06 (s, 1H); 7.36 (s, 1H); 8.15 (m, 1H); 8.35 (m, 1H).

Example 17

(5R)-5-ethyl-9,10-difluoro-5-hydroxy-12-(2-trimethylsilylethyl)-4,5,13,15-tetrahydro-1H,3H-oxepino[3',4':6,7]indolizino[1,2-b]quinoline-3,15-dione The product of Stage 13d is treated with 3-trimethylsilylpropanal (obtained according to Sarkar, T. K., et al., Tetrahedron (1990), vol. 46, p. 1885) according to a procedure similar to Stage 13e in order to produce the expected solid (m.p. 276° C.).

NMR $^1$H (DMSO-d$_6$, δ): 0.14 (s, 9H); 0.86 (m, 5H); 1.83 (q, 2H); 3.07 (m, 3H); 3.46 (d, 1H); 5.26 (s, 2H); 5.40 (d, 1H); 5.51 (d, 1H); 6.06 (s, 1H); 7.34 (s, 1H); 8.14 (m, 2H).

Example 18

(5R)-5-ethyl-9,11-difluoro-5-hydroxy-4,5,13,15-tetrahydro-1H,3H-oxepino[3',4':6,7]indolizino[1,2-b]quinoline-3,15-dione The operation is carried out with 3,5-difluoroaniline according to Stages 13a to 13c and the quinolylmethanol thus obtained is treated with (+)-EHHOPD according to the procedure of Stage 1h. A white solid is obtained (m.p. 227° C. (dec.)).

IR(KBr): 1638, 1748, 3310 cm$^{-1}$.

NMR $^1$H (DMSO-d$_6$, δ): 0.87 (t, 3H); 1.85 (q, 2H); 3.07 (d, 1H); 3.46 (d, 1H); 5.26 (s, 2H); 5.40 (d, 1H); 5.52 (d, 1H); 6.03 (s, 1H); 7.42 (s, 1H); 7.70 (t, 1H); 7.80 (d, 1H); 8.82 (s, 1H).

Example 19

(5R)-12-butyl-5-ethyl-9,11-difluoro-5-hydroxy-4,5,13,15-tetrahydro-1H,3H-oxepino[3',4':6,7]indolizino[1,2-b]quinoline-3,15-dione The product of Example 18 is treated with valeraldehyde according to a procedure similar to that of Stage 13e in order to produce the expected solid (m.p. 190° C.).
IR (KBr) 1657, 1751, 3385 cm$^{-1}$.
NMR $^1$H (DMSO-d$_6$, δ): 0.86 (t, 3H); 0.96 (t, 3H); 1.49 (q, 2H); 1.66 (q, 2H); 1.84 (q, 2H); 3.07 (d, 1H); 3.46 (d, 1H); 5.30 (s, 2H); 5.40 (d, 1H); 5.53 (d, 1H); 6.03 (s, 1H); 7.39 (s, 1H); 7.67 (t, 1H); 7.78 (d, 1H).

Example 20

(5R)-5,12-diethyl-9,11-difluoro-5-hydroxy-4,5,13,15-tetrahydro-1H,3H-oxepino[3',4':6,7]indolizino[1,2-b]quinoline-3,15-dione The product of Example 18 is treated with propionaldehyde according to a procedure similar to that in Stage 13e to produce the expected solid (m.p. 255° C.).
NMR $^1$H (DMSO-d$_6$, δ): 0.86 (t, 3H); 1.33 (t, 3H); 1.84 (q, 2H); 3.06 (d, 1H); 3.29 (m, 2H); 3.57 (d, 1H); 5.28 (s, 2H); 5.35 (d, 1H); 5.53 (d, 1H); 6.04 (s, 1H); 7.38 (s, 1H); 7.69 (m, 1H); 7.80 (m, 1H).

Example 21

(5R)-5-ethyl-5-hydroxy-12-propyl-4,5,13,15-tetrahydro-1H,3H-oxepino[3',4':6,7]indolizino[1,2-b]quinoline-3,15-dione (5R)-5-ethyl-5-hydroxy-4,5,13,15-tetrahydro-1H,3H-oxepino[3',4':6,7]indolizino [1,2-b]quinoline-3,15-dione (obtained according to the procedure described in the PCT Patent Application WO 97/00876) is treated with butyraldehyde according to a procedure similar to that of Stage 13e in order to produce the expected solid (m.p. 265° C. (dec.)).
IR (KBr): 1590, 1653, 3287 cm$^{-1}$.
NMR $^1$H (DMSO-d$_6$, δ): 0.87 (t, 3H); 1.06 (t, 3H); 1.73 (q, 2H); 1.82 (q, 2H); 3.06 (d, 1H); 3.19 (t, 2H); 3.48 (d, 1H); 5.24 (s, 2H); 5.31 (d, 1H); 5.54 (d, 1H); 6.02 (s, 1H); 7.38 (s, 1H); 7.72 (t, 1H); 7.85 (t, 1H); 8.15 (d, 1H); 8.28 (d, 1H).

Example 22

(5R)-5-ethyl-5-hydroxy-12-(2-trimethylsilylethyl)-4,5,13,15-tetrahydro-1H,3H-oxepino[3',4': 6,7]indolizino[1,2-b]quinoline-3,15-dione (5R)-5-ethyl-5-hydroxy-4,5,13,15-tetrahydro-1H,3H-oxepino[3',4':6,7]indolizino[1,2-b]quinoline-3,15-dione (obtained according to the procedure described in the PCT Patent Application WO 97/00876) is treated with 3-trimethylsilylpropanal (obtained according to Sarkar, T. K., et al., *Tetrahedron* (1990), vol. 46, p. 1885) according to a procedure similar to that of Stage 13e in order to produce the expected solid (m.p.>250° C.).
IR(KBr): 1655, 1753, 3420 cm$^{-1}$.
NMR $^1$H (DMSO-d$_6$, δ): 0.11 (s, 9H); 0.88 (t, 3H); 0.91 (m, 2H); 1.89 (q, 2H); 3.07 (d, 1H); 3.12 (m, 2H); 3.47 (d, 1H); 5.25 (s, 2H); 5.33 (d, 1H); 5.41 (d, 1H); 5.54 (d, 1H); 6.02 (s, 1H); 7.39 (s, 1H); 7.73 (t, 1H); 7.82 (s, 1H); 8.15 (s, 1H).

Example 23

(5R)-12-butyl-5-ethyl-9-fluoro-5-hydroxy-4,5,13,15-tetrahydro-1H,3H-oxepino[3',4':6,7]indolizino[1,2-b]quinoline-3,15-dione The product of Example 2 is treated with valeraldehyde according to a procedure similar to Stage 13e to produce the expected solid (m.p. 235–236° C.).
NMR $^1$H (DMSO-d$_6$, δ): 0.86 (t, 3H); 0.95 (t, 3H); 1.48 (m, 2H); 1.67 (m, 2H); 1.85 (q, 2H); 3.06 (d, 1H); 3.20 (t, 2H); 3.46 (d, 1H); 5.27 (s, 2H); 5.40 (d, 1H); 5.53 (d, 1H); 6.02 (s, 1H); 7.38 (s, 1H); 7.64 (t, 1H); 7.87 (d, 1H); 8.36 (dd, 1H).

Example 24

(5R)-5,12-diethyl-9-fluoro-5-hydroxy-4,5,13,15-tetrahydro-1H,3H-oxepino[3',4':6,7]indolizino[1,2-b]quinoline-3,15-dione The product of Example 2 is treated with propionaldehyde according to a procedure similar to Stage 13e in order to produce the expected solid.
NMR $^1$H (DMSO-d$_6$, δ): 0.86 (t, 3H); 1.31 (t, 3H); 1.85 (q, 2H); 3.06 (d, 1H); 3.22 (q, 2H); 3.47 (d, 1H); 5.24 (s, 2H); 5.39 (d, 1H); 5.53 (d, 1H); 6.03 (s, 1H); 7.38 (s, 1H); 7.64 (t, 1H); 7.87 (d, 1H); 8.37 (dd, 1H).

Example 25

(5R)-5-ethyl-5-hydroxy-12-isopentyl-4,5,13,15-tetrahydro-1H,3H-oxepino[3',4':6,7]indolizino[1,2-b]quinoline-3,15-dione 2-aminobenzonitrile is treated with isopentylmagnesium bromide according to a procedure similar to Stage 4a and the resulting amino-ketone is treated according to a procedure similar to Stage 4b. Stages 1f to 1h of the operating method of Example 1 above are applied to the quinolone obtained. A solid is obtained (m.p. 263° C.).
IR (KBr): 1655, 1743, 3343 cm$^{-1}$.
NMR $^1$H (DMSO-d$_6$, δ): 0.85 (t, 3H); 1.00 (d, 6H); 1.54 (m, 2H); 1.79 (m, 1H); 1.82 (m, 2H); 3.06 (4, 1H); 3.14 (m, 2H); 3.45 (d, 1H); 5.20 (s, 2H); 5.38 (d, 1H); 5.52 (d, 1H); 5.99 (s, 1H); 7.37 (s, 1H); 7.70 (t, 1H); 7.82 (t, 1H); 8.12 (d, 1H); 8.19 (d, 1H).

Example 26

(5R)-5-ethyl-12-(4-fluorophenyl)-5-hydroxy-4,5,13,15-tetrahydro-1H,3H-oxepino[3',4':6,7]indolizino[1,2-b]quinoline-3,15-dione 2-aminobenzonitrile is treated by 4-fluorophenylmagnesium bromide according to a procedure similar to Stage 4a and the resulting amino-ketone is treated according to a procedure similar to Stage 4b. Stages 1f to 1h of the operating method of Example 1 above are applied to the quinolone obtained.

Example 27

(5R)-12-(2,6-difluorophenyl)-5-ethyl-5-hydroxy-4,5,
13,15-tetrahydro-1H,3H-oxepino[3',4':6,7]indolizino
[1,2-b]quinoline-3,15-dione 2-aminobenzonitrile is treated by 2,6-difluorophenylmagnesium bromide according to a procedure similar to Stage 4a and the resulting amino-ketone is treated according to a procedure similar to Stage 4b. Stages 1f to 1h of the operating method of Example 1 above are applied to the quinolone obtained.

Example 28

(5R)-12-(3,5-difluorophenyl)-5-ethyl-5-hydroxy-4,5,
13,15-tetrahydro-1H,3H-oxepino[3',4':6,7]indolizino
[1,2-b]quinoline-3,15-dione 2-aminobenzonitrile is treated with 3,5-difluorophenylmagnesium bromide according to a procedure similar to Stage 4a and the resulting amino-ketone is treated according to a procedure similar to Stage 4b. Stages 1f to 1h of the operating method of Example 1 above are applied to the quinolone obtained.

Example 29

(5R)-5-ethyl-5-hydroxy-12-(3,4,5-trifluorophenyl)-4,
5,13,15-tetrahydro-1H,3H-oxepino[3',4':6,7]in-
dolizino[1,2-b]quinoline-3,15-dione 2-aminobenzonitrile is treated with 3,4,5-trifluorophenylmagnesium bromide according to a procedure similar to Stage 4a and the resulting amino-ketone is treated according to a procedure similar to Stage 4b. Stages 1f to 1h of the operating method of Example 1 above are applied to the quinolone obtained.

Example 30

(5R)-5-ethyl-5-hydroxy-12-(2,4,6-trifluorophenyl)-4,
5,13,15-tetrahydro-1H,3H-oxepino[3',4':6,7]in-
dolizino[1,2-b]quinoline-3,15-dione 2-aminobenzonitrile is treated with 2,4,6-trifluorophenylmagnesium bromide according to a procedure similar to Stage 4a and the resulting amino-ketone is treated according to a procedure similar to Stage 4b. Stages 1f to 1h of the operating method of Example 1 above are applied to the quinolone obtained.

Example 31

(5R)-5-ethyl-5-hydroxy-12-(2,3,5,6-tetrafluorophe-
nyl)-4,5,13,15-tetrahydro-1H,3H-oxepino[3',4':6,7]
indolizino[1,2-b]quinoline-3,15-dione 2-aminobenzonitrile is treated with 2,3,5,6-tetrafluorophenylmagnesium bromide according to a procedure similar to Stage 4a and the resulting amino-ketone is treated according to a procedure similar to Stage 4b. Stages 1f to 1h of the operating method of Example 1 above are applied to the quinolone obtained.

Example 32

(5R)-5-ethyl-5-hydroxy-12-(2,3,4,5,6-pentafluo-
rophenyl)-4,5,13,15-tetrahydro-1H,3H-oxepino[3',4':
6,7]indolizino[1,2-b]quinoline-3,15-dione 2-aminobenzonitrile is treated with 2,3,4,5,6-pentafluorophenylmagnesium bromide according to a procedure similar to Stage 4a and the resulting amino-ketone is treated according to a procedure similar to Stage 4b. Stages 1f to 1h of the operating method of Example 1 above are applied to the quinolone obtained.

Example 33

(5R)-5-ethyl-9-fluoro-12-(4-fluorophenyl)-5-hy-
droxy-4,5,13,15-tetrahydro-1H,3H-oxepino[3',4':6,7]
indolizino[1,2-b]quinoline-3,15-dione 2-amino-4-fluorobenzoic acid is treated according to a procedure similar to Stages 11a to 11c using 4-fluorophenylmagnesium bromide of Stage 11b, and the resulting aminoketone is treated according to a procedure similar to Stage 4b. Stages 1f to 1h of the operating method of Example 1 above are applied to the quinolone obtained.

NMR $^1$H (DMSO): 0.86 (t, 3H); 1.83 (q, 2H); 3.06 (d, 1H); 3.46 (d, 1H); 5.06 (dd, 2H); 5.37 (d, 1H); 5.49 (d, 1H); 6.04 (s, 1H); 7.43 (s, 1H); 7.52 (t, 2H); 7.60 (t, 1H); 7.73 (m, 2H); 7.83 (t. 1H); 7.97 (d, 1H).

Example 34

(5R)-12-(2,6-difluorophenyl)-5-ethyl-9-fluoro-5-
hydroxy-4,5,13,15-tetrahydro-1H,3H-oxepino[3',4':
6,7]indolizino[1,2-b]quinoline-3,15-dione 2-amino-4-fluorobenzoic acid is treated according to a procedure similar to Stages 11a to 11 c using 2,6-difluorophenyl magnesium bromide of Stage 11b, and the resulting aminoketone is treated according to a procedure similar to Stage 4b. Stages 1f to 1h of the operating method of Example 1 above are applied to the quinolone obtained.

Example 35

(5R)-12-(3,5-difluorophenyl)-5-ethyl-9-fluoro-5-
hydroxy-4,5,13,15-tetrahydro-1H,3H-oxepino[3',4':
6,7]indolizino[1,2-b]quinoline-3,15-dione 2-amino-4-fluorobenzoic acid is treated according to a procedure similar to Stages 11a to 11c using 3,5-difluorophenylmagnesium bromide of Stage 11b, and the resulting aminoketone is treated according to a procedure similar to Stage 4b. Stages 1f to 1h of the operating method of Example 1 above are applied to the quinolone obtained.

NMR $^1$H (DMSO): 0.86 (t, 3H); 1.84 (q, 2H); 3.06 (d, 1H); 3.47 (d, 1H); 5.15 (dd, 2H); 5.37 (d, 1H); 5.50 (d, 1H); 6.04 (s, 1H); 7.43 (s, 3H); 7.55 (t, 1H); 7.63 (t, 1H); 7.87 (t, 1H); 7.98 (d, 1H).

Example 36

(5R)-5-ethyl-9-fluoro-5-hydroxy-12-(3,4,5-trifluorophenyl)-4,5,13,15-tetrahydro-1H,3H-oxepino[3',4': 6,7]indolizino[1,2-b]quinoline-3,15-dione 2-amino-4-fluorobenzoic acid is treated according to a procedure similar to Stages 11a to 11c using 3,4,5-trifluorophenylmagnesium bromide of Stage 11b and the resulting amino-ketone is treated according to a procedure similar to Stage 4b. Stages 1f to 1h of the operating method of Example 1 above are applied to the quinolone obtained.

Example 37

(5R)-5-ethyl-9-fluoro-5-hydroxy-12-(2,4,6-trifluorophenyl)-4,5,13,15-tetrahydro-1H,3H-oxepino[3',4': 6,7]indolizino[1,2-b]quinoline-3,15-dione 2-amino-4-fluorobenzoic acid is treated according to a procedure similar to Stages 11a to 11c using 2,4,6-trifluorophenylmagnesium bromide of Stage 11b, and the resulting amino-ketone is treated according to a procedure similar to Stage 4b. Stages 1f to 1h of the operating method of Example 1 above are applied to the quinolone obtained.

Example 38

(5R)-5-ethyl-9-fluoro-5-hydroxy-12-(2,3,5,6-tetrafluorophenyl)-4,5,13,15-tetrahydro-1H,3H-oxepino[3',4':6,7]indolizino [1,2-b]quinoline-3,15-dione 2-amino-4-fluorobenzoic acid is treated according to a procedure similar to Stages 11a to 11c using 2,3,5,6-tetrafluorophenylmagnesium bromide of Stage 11b, and the resulting amino-ketone is treated according to a procedure similar to Stage 4b. Stages 1f to 1h of the operating method of Example 1 above are applied to the quinolone obtained.

Example 39

(5R)-5-ethyl-9-fluoro-5-hydroxy-12-(2,3,4,5,6-pentafluorophenyl)-4,5,13,15-tetrahydro-1H,3H-oxepino [3',4':6,7]indolizino [1,2-b]quinoline-3,15-dione 2-amino-4-fluorobenzoic acid is treated according to a procedure similar to Stages 11a to 11c using 2,3,4,5,6-pentafluorophenylmagnesium bromide of Stage 11b, and the resulting amino-ketone is treated according to a procedure similar to Stage 4b. Stages 1f to 1h of the operating method of Example 1 above are applied to the quinolone obtained.

Example 40

(5R)-5-ethyl-9,10-difluoro-12-(4-fluorophenyl)-5-hydroxy-4,5,13,15-tetrahydro-1H,3H-oxepino[3',4': 6,7]indolizino [1,2-b]quinoline-3,15-dione 2-amino-4,5-difluorobenzoic acid is treated according to a procedure similar to Stages 11a to 11c using 4-fluorophenylmagnesium bromide of Stage 11b, and the resulting amino-ketone is treated according to a procedure similar to Stage 4b. Stages 1f to 1h of the operating method of Example 1 above are applied to the quinolone obtained.

Example 41

(5R)-12-(2,6-difluorophenyl)-5-ethyl-9,10-difluoro-5-hydroxy-4,5,13,15-tetrahydro-1H,3H-oxepino[3', 4':6,7]indolizino[1,2-b]quinoline-3,15-dione 2-amino-4,5-difluorobenzoic acid is treated according to a procedure similar to Stages 11a to 11c using 2,6-difluorophenylmagnesium bromide of Stage 11b, and the resulting amino-ketone is treated according to a procedure similar to Stage 4b. Stages 1f to 1h of the operating method of Example 1 above are applied to the quinolone obtained.

Example 42

(5R)-12-(3,5-difluorophenyl)-5-ethyl-9,10-difluoro-5-hydroxy-4,5,13,15-tetrahydro-1H,3H-oxepino[3', 4':6,7]indolizino[1,2-b]quinoline-3,15-dione 2-amino-4,5-difluorobenzoic acid is treated according to a procedure similar to Stages 11a to 11c using 3,5-difluorophenylmagnesium bromide of Stage 11b, and the resulting amino-ketone is treated according to a procedure similar to Stage 4b. Stages 1f to 1h of the operating method of Example 1 above are applied to the quinolone obtained.

Example 43

(5R)-5-ethyl-9,10-difluoro-5-hydroxy-12-(3,4,5-trifluorophenyl)-4,5,13,15-tetrahydro-1H,3H-oxepino[3',4':6,7]indolizino[1,2-b]quinoline-3,15-dione 2-amino-4,5-difluorobenzoic acid is treated according to a procedure similar to Stages 11a to 11c using 3,4,5-trifluorophenylmagnesium bromide of Stage 11b, and the resulting amino-ketone is treated according to a procedure similar to Stage 4b. Stages 1f to 1h of the operating method of Example 1 above is applied to the quinolone obtained.

Example 44

(5R)-5-ethyl-9,10-difluoro-5-hydroxy-12-(2,4,6-trifluorophenyl)-4,5,13,15-tetrahydro-1H,3H-oxepino[3',4':6,7]indolizino[1,2-b]quinoline-3,15-dione 2-amino-4,5-difluorobenzoic acid is treated according to a procedure similar to Stages 11a to 11c using 2,4,6-trifluorophenylmagnesium bromide of Stage 11b, and the resulting amino-ketone is treated according to a procedure similar to Stage 4b. Stages 1f to 1h of the operating method of Example 1 above are applied to the quinolone obtained.

Example 45

(5R)-5-ethyl-9,10-difluoro-5-hydroxy-12-(2,3,5,6-tetrafluorophenyl)-4,5,13,15-tetrahydro-1H,3H-oxepino[3',4':6,7]indolizino[1,2-b]quinoline-3,15-dione 2-amino-4,5-difluorobenzoic acid is treated according to a procedure similar to Stages 11a to 11c using 2,3,5,6-tetrafluorophenylmagnesium bromide of Stage 11b, and the resulting amino-ketone is treated according to a procedure similar to Stage 4b. Stages 1f to 1h of the operating method of Example 1 above are applied to the quinolone obtained.

Example 46

(5R)-5-ethyl-9,10-difluoro-5-hydroxy-12-(2,3,4,5,6-pentafluorophenyl)-4,5,13,15-tetrahydro-1H,3H-oxepino[3',4':6,7]indolizino[1,2-b]quinoline-3,15-dione 2-amino-4,5-difluorobenzoic acid is treated according to a procedure similar to Stages 11a to 11c using 2,3,4,5,6-pentafluorophenylmagnesium bromide of Stage 11b, and the resulting amino-ketone is treated according to a procedure similar to Stage 4b. Stages 1f to 1h of the operating method of Example 1 above are applied to the quinolone obtained.

Example 47

(5R)-5-ethyl-9,11-difluoro-12-(4-fluorophenyl)-5-hydroxy-4,5,13,15-tetrahydro-1H,3H-oxepino[3',4':6,7]indolizino[1,2-b]quinoline-3,15-dione 2-amino-4,6-difluorobenzoic acid is treated according to a procedure similar to Stages 11a to 11c using 4-fluorophenylmagnesium bromide of Stage 11b, and the resulting amino-ketone is treated according to a procedure similar to Stage 4b. Stages 1f to 1h of the operating method of Example 1 above are applied to the quinolone obtained.

Example 48

(5R)-12-(2,6-difluorophenyl)-5-ethyl-9,11-difluoro-5-hydroxy-4,5,13,15-tetrahydro-1H,3H-oxepino[3',4':6,7]indolizino[1,2-b]quinoline-3,15-dione 2-amino-4,6-difluorobenzoic acid is treated according to a procedure similar to Stages 11a to 11c using 2,6-difluorophenylmagnesium bromide of Stage 11b, and the resulting amino-ketone is treated according to a procedure similar to Stage 4b. Stages 1f to 1h of the operating method of Example 1 above are applied to the quinolone obtained.

Example 49

(5R)-12-(3,5-difluorophenyl)-5-ethyl-9,11-difluoro-5-hydroxy-4,5,13,15-tetrahydro-1H,3H-oxepino[3',4':6,7]indolizino[1,2-b]quinoline-3,15-dione 2-amino-4,6-difluorobenzoic acid is treated according to a procedure similar to Stages 11a to 11c using 3,5-difluorophenylmagnesium bromide of Stage 11b, and the resulting amino-ketone is treated according to a procedure similar to Stage 4b. Stages 1f to 1h of the operating method of Example 1 above are applied to the quinolone obtained.

Example 50

(5R)-5-ethyl-9,11-difluoro-5-hydroxy-12-(3,4,5-trifluorophenyl)-4,5,13,15-tetrahydro-1H,3H-oxepino[3',4':6,7]indolizino[1,2-b]quinoline-3,15-dione 2-amino-4,6-difluorobenzoic acid is treated according to a procedure similar to Stages 11a to 11c using 3,4,5-trifluorophenylmagnesium bromide of Stage 11b, and the resulting amino-ketone is treated according to a procedure similar to Stage 4b. Stages 1f to 1h of the operating method of Example 1 above are applied to the quinolone obtained.

Example 51

(5R)-5-ethyl-9,11-difluoro-5-hydroxy-12-(2,4,6-trifluorophenyl)-4,5,13,15-tetrahydro-1H,3H-oxepino[3',4':6,7]indolizino[1,2-b]quinoline-3,15-dione 2-amino-4,6-difluorobenzoic acid is treated according to a procedure similar to Stages 11a to 11c using 2,4,6-trifluorophenylmagnesium bromide of Stage 11b, and the resulting amino-ketone is treated according to a procedure similar to Stage 4b. Stages 1f to 1h of the operating method of Example 1 above are applied to the quinolone obtained.

Example 52

(5R)-5-ethyl-9,11-difluoro-5-hydroxy-12-(2,3,5,6-tetrafluorophenyl)-4,5,13,15-tetrahydro-1H,3H-oxepino[3',4':6,7]indolizino[1,2-b]quinoline-3,15-dione 2-amino-4,6-difluorobenzoic acid is treated according to a procedure similar to Stages 11a to 11c using 2,3,5,6-tetrafluorophenylmagnesium bromide of Stage 11b, and the resulting amino-ketone is treated according to a procedure similar to Stage 4b. Stages 1f to 1h of the operating method of Example 1 above are applied to the quinolone obtained.

Example 53

(5R)-5-ethyl-9,11-difluoro-5-hydroxy-12-(2,3,4,5,6-pentafluorophenyl)-4,5,13,15-tetrahydro-1H,3H-oxepino[3',4':6,7]indolizino[1,2-b]quinoline-3,15-dione 2-amino-4,6-difluorobenzoic acid is treated according to a procedure similar to Stages 11a to 11c using 2,3,4,5,6-pentafluorophenylmagnesium bromide of Stage 11b, and the resulting amino-ketone is treated according to a procedure similar to Stage 4b. Stages 1f to 1h of the operating method of Example 1 above are applied to the quinolone obtained.

Example 54

(5R)-5-ethyl-9-fluoro-5-hydroxy-12-propyl-4,5,13,15-tetrahydro-1H,3H-oxepino[3',4':6,7]indolizino[1,2-b]quinoline-3,15-dione The product of Example 2 is treated with butyraldehyde according to a procedure similar to Stage 13e in order to produce the expected solid.

Example 55

(5R)-5-ethyl-9-fluoro-5-hydroxy-12-(3,3,3-trifluoropropyl)-4,5,13,15-tetrahydro-1H,3H-oxepino[3',4':6,7]indolizino[1,2-b]quinoline-3,15-dione The product of Example 2 is treated with 4,4,4-trifluorobutyraldehyde according to a procedure similar to Stage 13e in order to produce the expected solid.

Example 56

(5R)-5-ethyl-9-fluoro-5-hydroxy-12-isopentyl-4,5,13,15-tetrahydro-1H,3H-oxepino[3',4':6,7]indolizino[1,2-b]quinoline-3,15-dione The product of Example 2 is treated with 4-methylpentanal according to a procedure similar to Stage 13e in order to produce the expected solid.

Example 57

(5R)-5-ethyl-9-fluoro-5-hydroxy-12-pentyl-4,5,13,15-tetrahydro-1H,3H-oxepino[3',4':6,7]indolizino[1,2-b]quinoline-3,15-dione The product of Example 2 is treated with hexanal according to a procedure similar to Stage 13e in order to produce the expected solid.

Example 58

(5R)-5-ethyl-9-fluoro-5-hydroxy-12-phenethyl-4,5,13,15-tetrahydro-1H,3H-oxepino[3',4':6,7]indolizino[1,2-b]quinoline-3,15-dione The product of Example 2 is treated with 3-phenylpropanal according to a procedure similar to Stage 13e in order to produce the expected solid.
NMR $^1$H (DMSO): 0.86 (t, 3H); 1.84 (q, 2H); 3.02 (m, 2H); 3.07 (d, 1H); 3.44 (d, 1H); 3.51 (m, 2H); 5.01 (dd, 2H); 5.38 (d, 1H); 5.51 (d, 1H); 6.02 (s, 1H); 7.22 (m, 5H); 7.37 (s, 1H); 7.62 (m, 1H); 7.89 (dd, 1H); 8.40 (m, 1H).

Example 59

(5R)-12-decyl-5-ethyl-9-fluoro-5-hydroxy-4,5,13,15-tetrahydro-1H,3H-oxepino[3',4':6,7]indolizino[1,2-b]quinoline-3,15-dione The product of Example 2 is treated with undecanal according to a procedure similar to Stage 13e in order to produce the expected solid.

Example 60

(5R)-12-(2-cyclohexylethyl)-5-ethyl-9-fluoro-5-hydroxy-4,5,13,15-tetrahydro-1H,3H-oxepino[3',4':6,7]indolizino[1,2-b]quinoline-3,15-dione The product of Example 2 is treated with 3-cyclohexylpropanal according to a procedure similar to Stage 13e in order to produce the expected solid.

Example 61

(5R)-12-(3,3-dimethylbutyl)-5-ethyl-9-fluoro-5-hydroxy-4,5,13,15-tetrahydro-1H,3H-oxepino[3',4':6,7]indolizino[1,2-b]quinoline-3,15-dione The product of Example 2 is treated with 4,4-dimethylpentanal according to a procedure similar to Stage 13e in order to produce the expected solid.

Example 62

(5R)-5-ethyl-9,10-difluoro-5-hydroxy-12-propyl-4,5,13,15-tetrahydro-1H,3H-oxepino[3',4':6,7]indolizino[1,2-b]quinoline-3,15-dione The product of Stage 13d is treated with butyraldehyde according to a procedure similar to Stage 13e in order to produce the expected solid.

Example 63

(5R)-5-ethyl-9,10-difluoro-5-hydroxy-12-(3,3,3-trifluoropropyl)-4,5,13,15-tetrahydro-1H,3H-oxepino[3',4':6,7]indolizino[1,2-b]quinoline-3,15-dione The product of Stage 13d is treated with 4,4,4-trifluorobutyraldehyde according to a procedure similar to Stage 13e in order to produce the expected solid.

Example 64

(5R)-5-ethyl-9,10-difluoro-5-hydroxy-12-isopentyl-4,5,13,15-tetrahydro-1H,3H-oxepino[3',4':6,7]indolizino[1,2-b]quinoline-3,15-dione The product of Stage 13d is treated with 4-methylpentanal according to a procedure similar to Stage 13e in order to produce the expected solid.

Example 65

(5R)-5-ethyl-9,10-difluoro-5-hydroxy-12-pentyl-4,5,13,15-tetrahydro-1H,3H-oxepino[3',4':6,7]indolizino[1,2-b]quinoline-3,15-dione The product of Stage 13d is treated with hexanal according to a procedure similar to Stage 13e in order to produce the expected solid.

Example 66

(5R)-5-ethyl-9,10-difluoro-5-hydroxy-12-phenethyl-4,5,13,15-tetrahydro-1H,3H-oxepino[3',4':6,7]indolizino [1,2-b]quinoline-3,15-dione The product of Stage 13d is treated with 3-phenylpropanal according to a procedure similar to Stage 13e in order to produce the expected solid.

Example 67

(5R)-12-decyl-5-ethyl-9,10-difluoro-5-hydroxy-4,5,13,15-tetrahydro-1H,3H-oxepino[3',4':6,7]indolizino[1,2-b]quinoline-3,15-dione The product of Stage 13d is treated with undecanal according to a procedure similar to Stage 13e in order to produce the expected solid.

Example 68

(5R)-12-(2-cyclohexylethyl)-5-ethyl-9,10-difluoro-5-hydroxy-4,5,13,15-tetrahydro-1H,3H-oxepino[3',4':6,7]indolizino[1,2-b]quinoline-3,15-dione The product of Stage 13d is treated with 3-cyclohexylpropanal according to a procedure similar to Stage 13e in order to produce the expected solid.

Example 69

(5R)-12-(3,3-dimethylbutyl)-5-ethyl-9,10-difluoro-5-hydroxy-4,5,13,15-tetrahydro-1H,3H-oxepino[3',4':6,7]indolizino[1,2-b]quinoline-3,15-dione The product of Stage 13d is treated with 4,4-dimethylpentanal according to a procedure similar to Stage 13e in order to produce the expected solid.

Example 70

(5R)-5-ethyl-9,11-difluoro-5-hydroxy-12-propyl-4,5,13,15-tetrahydro-1H,3H-oxepino[3',4':6,7]indolizino[1,2-b]quinoline-3,15-dione The product of Example 18 is treated with butyraldehyde according to a procedure similar to Stage 13e in order to produce the expected solid.

Example 71

(5R)-5-ethyl-9,11-difluoro-5-hydroxy-12-(3,3,3-trifluoropropyl)-4,5,13,15-tetrahydro-1H,3H-oxepino[3',4':6,7]indolizino[1,2-b]quinoline-3,15-dione The product of Example 18 is treated with 4,4,4-trifluorobutyraldehyde according to a procedure similar to Stage 13e in order to produce the expected solid.

Example 72

(5R)-5-ethyl-9,11-difluoro-5-hydroxy-12-isopentyl-4,5,13,15-tetrahydro-1H,3H-oxepino[3',4':6,7]indolizino[1,2-b]quinoline-3,15-dione The product of Example 18 is treated with 4-methylpentanal according to a procedure similar to Stage 13e in order to produce the expected solid.

Example 73

(5R)-5-ethyl-9,11-difluoro-5-hydroxy-12-pentyl-4,5,13,15-tetrahydro-1H,3H-oxepino[3',4':6,7]indolizino[1,2-b]quinoline-3,15-dione The product of Example 18 is treated with hexanal according to a procedure similar to Stage 13e in order to produce the expected solid.

Example 74

(5R)-5-ethyl-9,11-difluoro-5-hydroxy-12-phenethyl-4,5,13,15-tetrahydro-1H,3H-oxepino[3',4':6,7]indolizino[1,2-b]quinoline-3,15-dione The product of Example 18 is treated with 3-phenylpropanal according to a procedure similar to Stage 13e in order to produce the expected solid.

Example 75

(5R)-12-decyl-5-ethyl-9,11-difluoro-5-hydroxy-4,5,13,15-tetrahydro-1H,3H-oxepino[3',4':6,7]indolizino[1,2-b]quinoline-3,15-dione The product of Example 18 is treated with undecanal according to a procedure similar to Stage 13e in order to produce the expected solid.

Example 76

(5R)-12-(2-cyclohexylethyl)-5-ethyl-9,11-difluoro-5-hydroxy-4,5,13,15-tetrahydro-1H,3H-oxepino[3',4':6,7]indolizino[1,2-b]quinoline-3,15-dione The product of Example 18 is treated with 3-cyclohexylpropanal according to a procedure similar to Stage 13e in order to produce the expected solid.

Example 77

(5R)-12-(3,3-dimethylbutyl)-5-ethyl-9,11-difluoro-5-hydroxy-4,5,13,15-tetrahydro-1H,3H-oxepino[3',4':6,7]indolizino[1,2-b]quinoline-3,15-dione The product of Example 18 is treated with 4,4-dimethylpentanal according to a procedure similar to Stage 13e in order to produce the expected solid.

Example 78

(5R)-12-chloro-5-ethyl-5-hydroxy-4,5,13,15-tetrahydro-1H,3H-oxepino[3',4':6,7]indolizino[1,2-b]quinoleine-3,15-dione Ethyl 2,4-dichloro-3-quinoleinecarboxylate (obtained according to *J Heterocyclic Chem.*, 35, 627 (1998)) is treated according to a procedure similar to Stages 1g to 1h of the operating method of Exemple 1 above.

NMR $^1$H (DMSO): 0.87 (t, 3H); 1.85 (q, 2H); 3.07 (d, 1H); 3.46 (d, 1H); 5.27 (s, 2H); 5.40 (d, 1H); 5.52 (d, 1H); 6.03 (s, 1H); 7.41 (s, 1H); 7.86 (t, 1H); 7.97 (t, 1H); 8.22 (d, 1H); 8.30 (d, 1H).

Example 79

(5R)-5-ethyl-5-hydroxy-12-hydroxymethyl-4,5,13,15-tetrahydro-1H,3H-oxepino[3',4':6,7]indolizino[1,2-b]quinoleine-3,15-dione (5R)-5-ethyl-5-hydroxy-4,5,13,15-tetrahydro-1H,3H-oxepino[3',4':6,7]indolizino[1,2-b]quinoleine-3,15-dione (obtained according to the procedure described in the patent application WO 97/00876) is treated with methanol according to a procedure similar to Stage 13e in order to produce the expected compound.

NMR $^1$H (DMSO): 0.87 (t, 3H); 1.85 (q, 2H); 3.08 (d, 1H); 3.44 (d, 1H); 5.19 (d, 2H); 5.38 (m, 3H); 5.52 (d, 1H); 5.80 (m, 1H); 5.98 (s, 1H); 7.38 (s, 1H); 8.15 (m, 1H); 8.23 (m, 1H).

Example 80

(5R)-5-ethyl-9-fluoro-5-hydroxy-12-isobutyl-4,5,13,15-tetrahydro-1H,3H-oxepino[3',4':6,7]indolizino[1,2-b]quinoleine-3,15-dione The product of Example 2 is treated with 3-methylbutanal according to a procedure similar to Stage 13e in order to produce the expected compound.

NMR $^1$H (DMSO): 0.86 (t, 3H); 0.98 (d, 6H); 1.84 (q, 2H); 2.11 (m, 1H); 3.05 (d, 1H); 3.12 (m, 2H); 3.46 (d, 1H); 5.25 (dd, 2H); 5.39 (d, 1H); 5.52 (d, 1H) 6.02 (s, 1H); 7.39 (s, 1H); 7.65 (m, 1H); 7.87 (dd, 1H); 8.37 (m, 1H).

Example 81

(5R)-5-ethyl-9-fluoro-5-hydroxy-12-neopentyl-4,5,13,15-tetrahydro-1H,3H-oxepino[3',4':6,7]indolizino[1,2-b]quinoleine-3,15-dione The product of Example 2 is treated with 3,3-dimethylbutanal according to a procedure similar to Stage 13e in order to produce the expected compound.

NMR $^1$H (DMSO): 0.86 (t, 3H); 1.01 (s, 9H); 1.84 (q, 2H); 3.05 (d, 1H); 3.22 (m, 2H); 3.46 (d, 1H); 5.26 (dd, 2H); 5.38 (d, 1H); 5.52 (d, 1H); 6.01 (s, 1H); 7.39 (s, 1H); 7.60 (m, 1H); 7.85 (dd, 1H); 8.46 (m, 1H).

Example 82

(5R)-5-ethyl-9-fluoro-12-(3-fluorophenyl)-5-hydroxy-4,5,13,15-tetrahydro-1H,3H-oxepino[3',4':6,7]indolizino[1,2-b]quinoleine-3,15-dione 2-amino-4-fluorobenzoic acid is treated according to a procedure similar to Stages 11a to 11c using 3-fluorophenylmagnesium bromide of Stage 11b, and the resulting aminoketone is treated according to a procedure similar to Stage 4b. Stages 1f to 1h of the operating method of Example 1 above are applied to the quinolone obtained.

NMR $^1$H (DMSO): 0.86 (t, 3H); 1.84 (q, 2H); 3.06 (d, 1H); 3.46 (d, 1H); 5.08 (m, 2H); 5.37 (d, 1H); 5.49 (d, 1H); 6.04 (s, 1H); 7.43 (s, 1H); 7.48 (m, 2H); 7.61 (m, 2H); 7.73 (m, 1H); 7.83 (m, 1H); 7.97 (m, 1H).

Example 83

(5R)-5-ethyl-9-fluoro-5-hydroxy-12-(4-trifluoromethyl phenyl)-4,5,13,15-tetrahydro-1H,3H-oxepino[3',4':6,7]indolizino [1,2-b]quinoleine-3,15-dione 2-amino-4-fluorobenzoic acid is treated according to a procedure similar to Stages 11a to 11c using 4-trifluoromethylphenylmagnesium bromide of Stage 11b, and the resulting amino-ketone is treated according to a procedure similar to Stage 4b. Stages 1f to 1h of the operating method of Example 1 above are applied to the quinolone obtained.

NMR $^1$H (DMSO): 0.86 (t, 3H); 1.83 (q, 2H); 3.06 (d, 1H); 3.46 (d, 1H); 5.06 (dd, 2H); 5.37 (d, 1H); 5.49 (d, 1H); 6.04 (s, 1H); 7.43 (s, 1H); 7.52 (t, 2H); 7.60 (t, 2H); 7.73 (m, 2H); 7.83 (t, 1H); 7.97 (d, 1H).

Example 84

(5R)-5-ethyl-9-fluoro-5-hydroxy-12-(4-trifluoromethoxy phenyl)-4,5,13,15-tetrahydro-1H,3H-oxepino[3',4':6,7]indolizino [1,2-b]quinoleine-3,15-dione 2-amino-4-fluorobenzoic acid is treated according to a procedure similar to Stages 11a to 11c using 4-trifluoromethoxyphenylmagnesium bromide of Stage 11b, and the resulting amino-ketone is treated according to a procedure similar to Stage 4b. Stages 1f to 1h of the operating method of Example 1 above are applied to the quinolone obtained.

NMR $^1$H (DMSO): 0.86 (t, 3H); 1.83 (q, 2H); 3.06 (d, 1H); 3.46 (d, 1H); 5.06 (dd, 2H); 5.37 (d, 1H); 5.49 (d, 1H); 6.03 (s, 1H); 7.43 (s, 1H); 7.59 (m, 1H); 7.68 (m, 2H); 7.81 (m, 1H); 7.97 (dd, 1H).

Example 85

(5R)-12-(4-dimethylaminophenyl)-5-ethyl-9-fluoro-5-hydroxy-4,5,13,15-tetrahydro-1H,3H-oxepino[3',4':6,7]indolizino[1,2b]quinoleine-3,15-dione 2-amino-4-fluorobenzoic acid is treated according to a procedure similar to Stages 11a to 11c using 4-dimethylaminophenylmagnesium chloride of Stage 11b, and the resulting amino-ketone is treated according to a procedure similar to Stage 4b. Stages 1f to 1h of the operating method of Example 1 above are applied to the quinolone obtained.

NMR $^1$H (DMSO): 0.86 (t, 3H); 1.84 (q, 2H); 3.04 (s, 6H); 3.06 (d, 1H); 3.46 (d, 1H); 5.10 (dd, 2H); 5.36 (d, 1H); 5.49 (d, 1H); 6.02 (s, 1H); 6.95 (d, 2H); 7.40 (s, 1H); 7.49 (d, 2H); 7.57 (t, 1H); 7.90 (d, 1H); 8.01 (t, 1H).

Example 86

(5R)-12-[4-(tert-butyl)phenyl]-5-ethyl-9-fluoro-5-hydroxy-4,5,13,15-tetrahydro-1H,3H-oxepino[3',4':6,7]indolizino[1,2-b]quinoleine-3,15-dione 2-amino-4-fluorobenzoic acid is treated according to a procedure similar to Stages 11a to 11c using 4-tert-butylphenylmagnesium bromide of Stage 11b, and the resulting aminoketone is treated according to a procedure similar to Stage 4b. Stages 1f to 1h of the operating method of Example 1 above are applied to the quinolone obtained.

NMR $^1$H (DMSO): 0.86 (t, 3H); 1.40 (s, 9H); 1.85 (q, 2H); 3.05 (d, 1H); 3.47 (d, 1H); 5.08 (dd, 2H); 5.37 (d, 1H); 5.49 (d, 1H); 6.04 (s, 1H); 7.44 (s, 1H); 7.60 (m, 3H); 7.69 (d, 2H); 7.89 (m, 1H); 7.96 (m, 1H).

Example 87

(5R)-5-ethyl-9,11-difluoro-5-hydroxy-12-propyl-4,5,13,15-tetrahydro-1H,3H-oxepino[3',4':6,7]indolizino[1,2-b]quinoleine-3,15-dione The product of Example 18 is treated with butyraldehyde according to a procedure similar to Stage 13e in order to produce the expected compound.

NMR $^1$H (DMSO): 0.86 (t, 3H); 1.04 (t, 3H); 1.70 (q, 2H); 1.84 (q, 2H); 3.05 (d, 1H); 3.14 (m, 2H); 3.47 (d, 1H); 5.25 (dd, 2H); 5.35 (d, 1H); 5.52 (d, 1H); 6.07 (s, 1H); 7.38 (s, 1H); 7.67 (m, 1H); 7.78 (m, 1H).

Example 88

(5R)-12-(2-ethoxyethyl)-5-ethyl-9,11-difluoro-5-hydroxy-4,5,13,15-tetrahydro-1H,3H-oxepino[3',4': 6,7]indolizino[1,2-b]quinoleine-3,15-dione The product of Example 18 is treated with 3-ethoxypropanal according to a procedure similar to Stage 13e in order to produce the expected compound.

NMR $^1$H (DMSO): 0.86 (t, 3H); 1.05 (t, 3H); 1.84 (q, 2H); 3.07 (d, 1H); 3.43 (m, 5H); 3.77 (t, 2H); 5.26 (dd, 2H); 5.39 (d, 1H); 5.52 (d, 1H); 6.03 (s, 1H); 7.39 (s, 1H); 7.67 (m, 1H); 7.79 (dd, 1H).

Example 89

(5R)-5-ethyl-9,10,11-trifluoro-5-hydroxy-4,5,13,15-tetrahydro-1H,3H-oxepino[3',4':6,7]indolizino[1,2-b]quinoleine-3,15-dione Stages 13a to 13c are applied to 3,4,5-trifluoroaniline and the resulting quinolylmethanol is treated with (+)-EHHOPD according to a procedure of Stage 1h in order to produce the expected compound.

NMR $^1$H (DMSO): 0.87 (t, 3H); 1.83 (q, 2H); 3.07 (d, 1H); 3.45 (d, 1H); 5.26 (s, 2H); 5.39 (d, 1H); 5.51 (d, 1H); 6.03 (s, 1H); 7.40 (s, 1H); 8.09 (m, 1H); 8.86 (s, 1H).

Example 90

(5R)-5-ethyl-9-fluoro-5-hydroxy-3,15-dioxo-4,5,13, 15-tetrahydro-1H,3H-oxepino[3',4':6,7]indolizino[1, 2-b]quinolein-10-yl trifluorometanesulfonate (5R)-5-ethyl-9-fluoro-5,10-dihydroxy-4,5,13,15-tetrahydro-1H,3H-oxepino-[3',4':6,7]indolizino[1,2-b]quinoleine-3,15-dione (28 mg, obtained according to the preparation 20 described in the patent application WO 98/28304) in anhydrous DMF solution (5 ml) is traited at 0° C. with 1.1 equivalent of sodium hydride, then with 1.1 equivalent of N-phenyltrifluorosulfonimide. The reaction medium is maintained under agitation for 2 h at ambient temperature, then poured into iced water and extracted with ethyl. The organic phase is dried and concentrated then the residue is taken up in ether and recovered by filtration to produce the expected compound.

NMR $^1$H (DMSO): 0.87 (t, 3H); 1.86 (q, 2H); 3.07 (d, 1H); 3.46 (d, 1H); 5.29 (s, 1H); 5.40 (d, 1H); 5.52 (d, 1H); 6.04 (s, 1H); 7.43 (s, 1H); 8.31 (d, 1H); 8.66 (d, 1H); 8.82 (s, 1H).

Pharmacological Study of the Products of the Invention

Procedure

Adenocarcinoma HT29 cells from the human colon are cultured in a single layer at 37° C. in a humidified atmosphere containing 95% of air and 5% of $CO_2$, in a modified essential Earle's medium at 4.5 g/l (Gibco, Paisley, United Kingdom); completed with 10% of inactivated foetal calf serum, 2 mM of glutamine, and 50 µg/ml of gentamycin (Gibco, Paisley, United Kingdom).

Approximately 2000 cells are seeded with the culture medium above in the wells of a microplate (96 wells, flat-bottomed) and incubated for 24 hours. Solutions in N,N-dimethyl-acetamide (DMA) of each of the examples of the invention, diluted in the culture medium so that the final concentration of DMA is 0.1% (v/v), are added to the plate cultures in order to obtain final concentration ranges from $1 \times 10^{-13}$ to $1 \times 10^{-5}$ M, and the cells are incubated for 72 hours.

The WST1 staining reagent, (Boehringer Mannheim, Germany) is then added to each well at a final concentration of 9%, and the cells are incubated for 2 hours at 37° C. This stage allows the mitochondrial deshydrogenase of the living cells to convert WST1 orange tetrazolium salt into crimson formazan. The resulting stained solutions are quantified by dual-beam detection (450 and 690 nm) using a multi-cuvette scanning spectrophotometer.

Results

The results shown in the following table are expressed in terms of inhibitory concentration at 50% ($IC_{50}$, in nM), accompanied by a confidence interval. The inhibitory activities of the adenocarcinoma HT29 cell proliferation of the human colon obtained with the examples of the invention are assessed, these activities being, in an unexpected fashion, superior to the activity of the reference compound (corresponding to a compound of formula $I_A$ wherein $R_1=R_2=R_3=R_4=R_5=R_6=H$) described in the PCT Patent Application WO 97/000876.

| | Biological activity | |
|---|---|---|
| Reference | $IC_{50}$ (nM) 30 | Confidence interval 24–39 |
| 2 | 2.5 | 1.0–7.2 |
| 5 | 16 | 11–23 |
| 6 | 12 | 9–14 |
| 7 | 13 | 8–19 |
| 9 | 11 | 8–15 |
| 11 | 12 | 7–21 |
| 13 | 8.5 | 4–16 |
| 15 | 11 | 7–17 |
| 16 | 2.1 | 1.5–2.7 |
| 17 | 5.0 | 1.7–16 |
| 18 | 2.2 | 1.4–3.3 |
| 20 | 8 | 4.7–15 |
| 22 | 8.6 | 3–26 |
| 23 | 9.5 | 5–17 |
| 24 | 3.5 | 2.3–5.4 |
| 33 | 0.26 | 0.04–0.65 |
| 35 | 0.25 | |
| 58 | 3.2 | 1.8–5.3 |
| 78 | 5.5 | 4.2–7.1 |
| 80 | 12 | 8.5–17 |
| 81 | 6 | |
| 82 | 2.7 | 1.5–4.8 |
| 83 | 1.7 | 0.6–5 |
| 84 | 8.9 | 5.2–15 |
| 85 | 13 | 7–23 |
| 87 | 2.3 | 1.6–3.4 |
| 88 | 0.85 | 0.38–7.1 |
| 89 | 8.2 | 5.1–13 |

What is claimed is:

1. A compound which is (5R)-5-ethyl-9,10,difluoro-5-hydroxy-12-(2-trimethylsilylethyl)-4,5,13,15-tetrahydro-1H,3H-oxepino[3',4':6,7]-indoloizino[1,2-b]quinoleine-3,15-dione.

2. A pharmaceutical composition comprising an antitumorally effective amount of a compound of formula ($II_A$) of claim 1 and an inert carrier.

3. A method of treating colon cancer in warm-blooded animals comprising administering to warm-blooded animals in need thereof an effective amount of a compound of claim 1 to treat colon cancer.

* * * * *